(12) United States Patent
Benelhadj et al.

(10) Patent No.: US 10,734,591 B2
(45) Date of Patent: Aug. 4, 2020

(54) MOLECULES PRESENTING DUAL EMISSION PROPERTIES

(71) Applicants: Université de Strasbourg, Strasbourg (FR); UNIVERSITE DE NANTES, Nantes (FR); Centre national de la recherche scientifque, Paris (FR)

(72) Inventors: Karima Benelhadj, Strasbourg (FR); Julien Massue, Strasbourg (FR); Gilles Ulrich, Souffelweyersheim (FR); Raymond Ziessel, Souffelweyersheim (FR); Denis Jacquemin, Nantes (FR); Adèle Laurent, Nantes (FR)

(73) Assignees: UNIVERSITÉ DE STRASBOURG, Strasbourg (FR); UNIVERSITE DE NANTES, Nantes (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 117 days.

(21) Appl. No.: 15/327,932

(22) PCT Filed: Jul. 21, 2015

(86) PCT No.: PCT/EP2015/066664
§ 371 (c)(1),
(2) Date: Jan. 20, 2017

(87) PCT Pub. No.: WO2016/012457
PCT Pub. Date: Jan. 28, 2016

(65) Prior Publication Data
US 2017/0207400 A1 Jul. 20, 2017

(30) Foreign Application Priority Data
Jul. 21, 2014 (EP) .................................. 14306182

(51) Int. Cl.
*C07D 307/79* (2006.01)
*C07D 307/80* (2006.01)
(Continued)

(52) U.S. Cl.
CPC ........ *H01L 51/0073* (2013.01); *C07D 307/79* (2013.01); *C07D 307/80* (2013.01);
(Continued)

(58) Field of Classification Search
None
See application file for complete search history.

(56) References Cited
U.S. PATENT DOCUMENTS
4,482,629 A  11/1984 Nakagawa et al.
4,889,924 A  12/1989 Akasaki et al.
(Continued)

FOREIGN PATENT DOCUMENTS
JP  A-1983162949  9/1983
JP  59149361  8/1984
(Continued)

OTHER PUBLICATIONS

Renhowe, P.A. et al. "Design, Structure-Activity Relationships and in Vivo Characterization of 4-Amino-3-benzimidazol-2-ylhydroquinolin-2-ones: A Novel Class of Receptor Tyrosine Kinase Inhibitors," J. Med. Chem. 2009, 52, 278-292. (Year: 2009).*

(Continued)

*Primary Examiner* — Christopher Adam Hixson
*Assistant Examiner* — Michelle Adams
(74) *Attorney, Agent, or Firm* — B. Aaron Schulman, Esq.; Stites & Harbison, PLLC

(57) ABSTRACT

A compound is provided which has dual emission properties and which is useful in light devices, and which has formula (I):

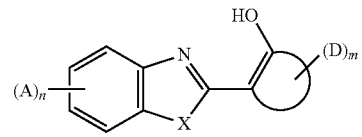

wherein:
A represents an electron-withdrawing group;
D represents an electron-donating group;
X is selected from the group consisting of: O, S and NR, wherein R is selected from the group consisting of: H, an alkyl group preferably comprising from 1 to 20 carbon atoms, an aryl group preferably comprising from 6 to 22 carbon atoms, and a heteroaryl group;
n is an integer from 1 to 4;
m is an integer from 1 to 6; and

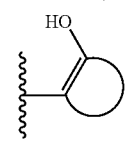

represents a condensed bicyclic aromatic radical comprising from 6 to 22 carbon atoms, and from 1 to 3 heteroatom(s) selected from the group consisting of: N, S and O;
the OH group being in ortho position of the condensed bicyclic aromatic radical relative to the

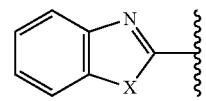

radical.

25 Claims, 8 Drawing Sheets

(51) Int. Cl.
| | |
|---|---|
| C07D 307/81 | (2006.01) |
| H01L 51/00 | (2006.01) |
| H01L 51/50 | (2006.01) |
| C09K 11/06 | (2006.01) |
| C09B 57/00 | (2006.01) |
| C07D 413/04 | (2006.01) |
| C07D 413/14 | (2006.01) |
| C07D 417/04 | (2006.01) |

(52) U.S. Cl.
CPC ......... *C07D 307/81* (2013.01); *C07D 413/04* (2013.01); *C07D 413/14* (2013.01); *C07D 417/04* (2013.01); *C09B 57/00* (2013.01); *C09K 11/06* (2013.01); *H01L 51/0071* (2013.01); *H01L 51/5012* (2013.01); *C09K 2211/1007* (2013.01); *C09K 2211/1033* (2013.01); *C09K 2211/1037* (2013.01); *C09K 2211/1088* (2013.01)

(56) References Cited

U.S. PATENT DOCUMENTS

| | | | |
|---|---|---|---|
| 5,587,112 | A | 12/1996 | Kauffman et al. |
| 6,756,383 | B2 | 6/2004 | Renhowe et al. |
| 6,759,417 | B2 | 7/2004 | Renhowe et al. |
| 6,867,200 | B1 | 3/2005 | Allen et al. |
| 7,138,409 | B2 | 11/2006 | Renhowe et al. |
| 7,368,459 | B2 | 5/2008 | Renhowe et al. |
| 2002/0103230 | A1 | 8/2002 | Renhowe et al. |
| 2003/0028018 | A1 | 2/2003 | Renhowe et al. |
| 2004/0002518 | A1 | 1/2004 | Renhowe et al. |
| 2005/0137188 | A1 | 6/2005 | Renhowe et al. |
| 2005/0137399 | A1 | 6/2005 | Cai et al. |
| 2005/0209247 | A1 | 9/2005 | Cai et al. |
| 2007/0032528 | A1 | 2/2007 | Renhowe et al. |
| 2008/0070906 | A1 | 3/2008 | Renhowe et al. |
| 2009/0181979 | A1 | 7/2009 | Cai et al. |
| 2010/0184754 | A1 | 7/2010 | Renhowe et al. |
| 2012/0277434 | A1 | 11/2012 | Cai et al. |
| 2013/0018058 | A1 | 1/2013 | Cai et al. |
| 2013/0338171 | A1 | 12/2013 | Cai et al. |
| 2014/0303182 | A1 | 10/2014 | Cai et al. |

FOREIGN PATENT DOCUMENTS

| | | |
|---|---|---|
| JP | A-1988089570 | 4/1988 |
| JP | 2003147344 A * | 5/2003 |
| JP | 2006251327 | 9/2006 |

OTHER PUBLICATIONS

El-Desoky I El-Saved et al: "Synthesis of Some Chromanone Derivatives and the Use of DNA in Evaluation of their Biological Activity", Zeitschrift Fur Natruforschung B, vol. 53, Jan. 1, 1998 (Jan. 1, 1998), pp. 909-915, XP055148964, ISSN: 0932-0776 * scheme 2, compound 8b *.
Massue Julien et al: "Fluorescent 2-(2'-hydroxybenzofuran)benzoxazole (HBBO) borate complexes: synthesis, optical properties, and theoretical calculat", Tetrahedron Letters, vol. 55, No. 30, Jun. 9, 2014 (Jun. 9, 2014), pp. 4136-4140, XP028861805, ISSN: 0040-4039, DOI: 10.1016/J.TETLET.2014.06.002 * the whole document *.
Klymchenko A S et al: "A 3-hydroxychronpne with dramatically improved fluorescence properties", Tetrahedron Letters, Pergamon, GB, vol. 42, No. 45, Nov. 5, 2001 (Nov. 5, 2001), pp. 7967-7970, XP004309963, ISSN: 0040-4039, DOI: 10.1016/s0040-4039 (01)01723-3* the whole document*.
European Search Report for EP 14306182, completed Oct. 28, 2014.
International Search Report for PCT/EP2015/066664, completed Aug. 26, 2015.
Written Opinion of the International Searching Authority for PCT/EP2015/066664, completed Aug. 26, 2015.
Feng, et al., "Palladium-Catalyzed Trifluoroethylation of Terminal Alkynes with 1,1,1-Trifluoro-2-iodoethane", 2013, pp. 936-939, vol. 15, No. 4, Org. Lett.
Miller, et al., "Synthesis and Optical Properties of Donor-Acceptor Tetrakis(Phenyl-ethynyl)benzenes", 2004, pp. 0165-0168, No. 1, Synlett.
Benelhadj, et al., "White Emitters by Tuning the Excited-State Intramolecular Proton-Transfer Fluorescence Emission in 2-(2'-Hydroxybenzofuran) benzoxazole Dyes", 2014, pp. 12843-12857, vol. 20, Chem. Eur.
Database Registry 2008, RN 1026709-86-3.
Database Registry 2008, RN 1027422-62-3.
Wang, et al., "Substituent and solvent effects on excited state intramolecular proton transfer in novel 2-(2'-hydroxyphenyl) benzothiazole derivatives", 2009, pp. 61-69, Journal of Photochemistry and Photobiology A: Chemistry.
Padalkar, et al., "Synthesis and Photo-Physical Characteristics of ESIPT Inspried 2-Substituted Benzimidazole, Benzoxazole and Benzothiazole Fluorescent Derivatives", 2012, pp. 311-322, vol. 22, J Fluorence.
El-Sayed, et al, "Synthesis of Some Chromanone Derivatives and the Use of DNA in Evaluation of their Biological Activity", 1998, pp. 909-915, vol. 53b.
Miller, et al, "Synthesis and Optical Properties of Donor-Acceptor Tetrakis(phenyl-ethynyl)benzenes", 2004, pp. 165-168, No. 1, Synlett.

* cited by examiner

MOLECULES PRESENTING DUAL EMISSION PROPERTIES

CROSS-REFERENCE TO RELATED APPLICATIONS

This patent application is a national stage application under 35 U.S.C. 371 of PCT application PCT/EP2015/066664 which claims the priority of the European patent application EP 14306182.8.

FIELD OF THE INVENTION

The present invention relates to new molecules exhibiting dual emission properties, and more particularly white light emission properties, and their method of preparation.

The present invention also concerns their applications, notably as fluorescent probes in ratiometric detection, or white light emitting sources.

BACKGROUND OF THE INVENTION

Fluorescent probes are typically used for qualitative and/or quantitative titrations in various fields such as immunology, molecular biology, medical diagnostic . . . . An ideal condition for a compound to be used as fluorescent probe, and thus allow the titration of a target analyte, is to display dual emission properties varying depending upon the conditions (presence or not of the analyte, pH . . . ). Such compounds allow, for example, ratiometric titrations leading to the determination of the analyte concentration, whatever the fluorescent probe concentration.

In the field of luminescent devices, the use of compounds having dual emission properties can lead to the production of polychromatic fluorescence such as white light, without requiring several polychromatic emitters.

Only few systems using a single molecule are known to exhibit dual emission.

However, dual emission, and more particularly white light emission, from a single molecule is an important chemical target because of the possibility of innovative applications to new classes of displays and light sources, such as low-cost, large-area flat-panel displays. Most of the white organic light-emitting devices (WOLEDs) reported so far relied on the use of a combination of several organic components that emit different colors of light (e.g. red/blue/green luminophores) to cover the visible range from 400 to 700 nm.

Therefore, the search for new molecules that can exhibit dual emission properties, and more particularly white light emission properties, is of obvious interest and importance.

AIM OF THE INVENTION

One aim of the present invention is to provide new compounds with dual emission properties, more particularly in solution and/or in solid state.

Another aim of the present invention is to provide new white light emitting compounds.

One aim of the present invention is to provide new compounds displaying broad and tunable dual emission.

The present invention also aims to provide such compounds with good luminescent properties, such as fluorescent or electroluminescent properties.

The present invention aims to provide such compounds with acceptable quantum yields.

The present invention also aims to provide devices for ratiometric detection.

The present invention also aims to provide devices emitting white light.

SUMMARY OF THE INVENTION

The present invention concerns a compound of formula (I):

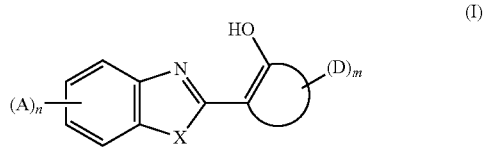

wherein:
A represents an electron-withdrawing group;
D represents an electron-donating group;
X is selected from the group consisting of: O, S and NR, wherein R is selected from the group consisting of: H, an alkyl group preferably comprising from 1 to 20 carbon atoms, an aryl group preferably comprising from 6 to 22 carbon atoms, and a heteroaryl group;
n is an integer from 1 to 4;
m is an integer from 1 to 6, preferably from 1 to 4;

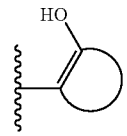 [SMILES: */C=C\O]

represents a condensed bicyclic aromatic radical comprising from 6 to 22 carbon atoms, and optionally from 1 to 3 heteroatom(s) selected from the group consisting of: N, S and O;
the OH group being in ortho position of the condensed bicyclic aromatic radical relative to the

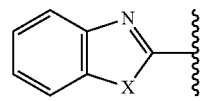

radical.

DETAILED DESCRIPTION OF THE INVENTION

Figure 1:
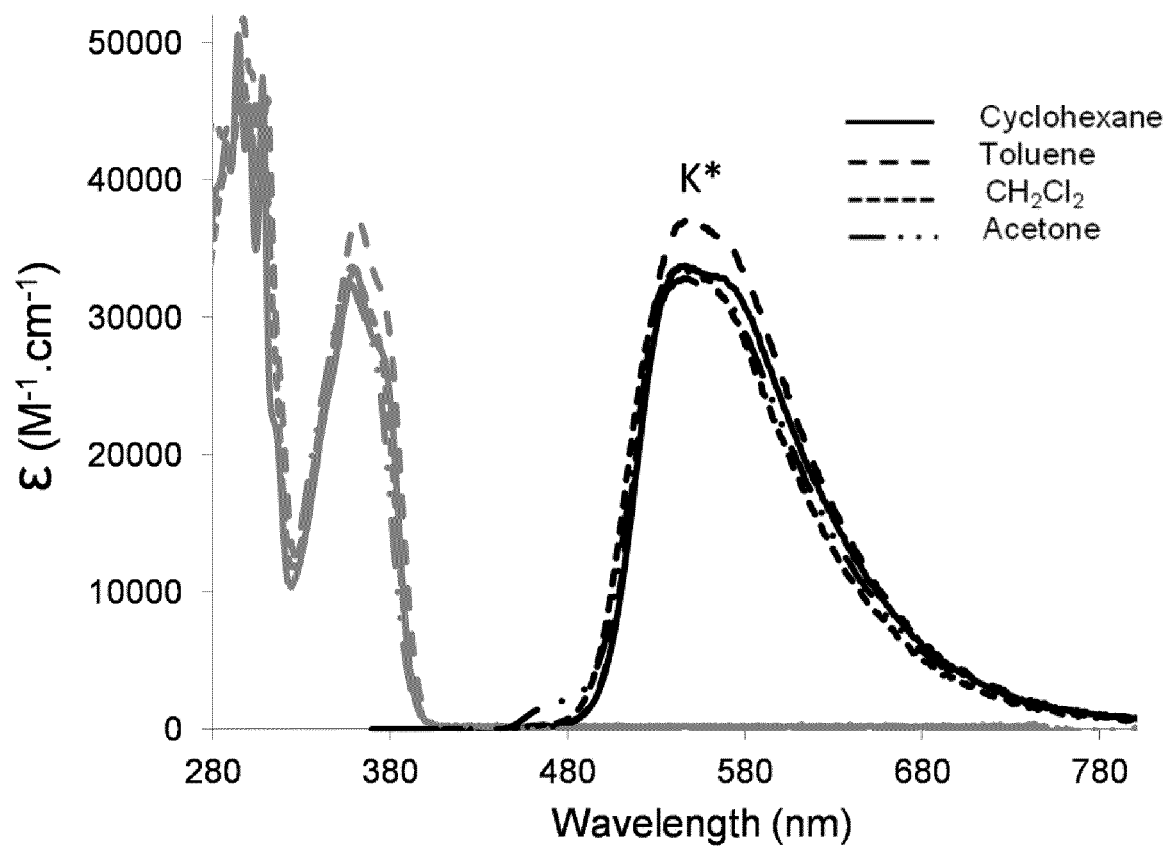
FIG. 1 corresponds to the absorption (in grey) and emission spectra (in black) in various solvents for comparative compound 5. Such data were recorded at room temperature (25° C.). Only K* band appears.
Figure 2:
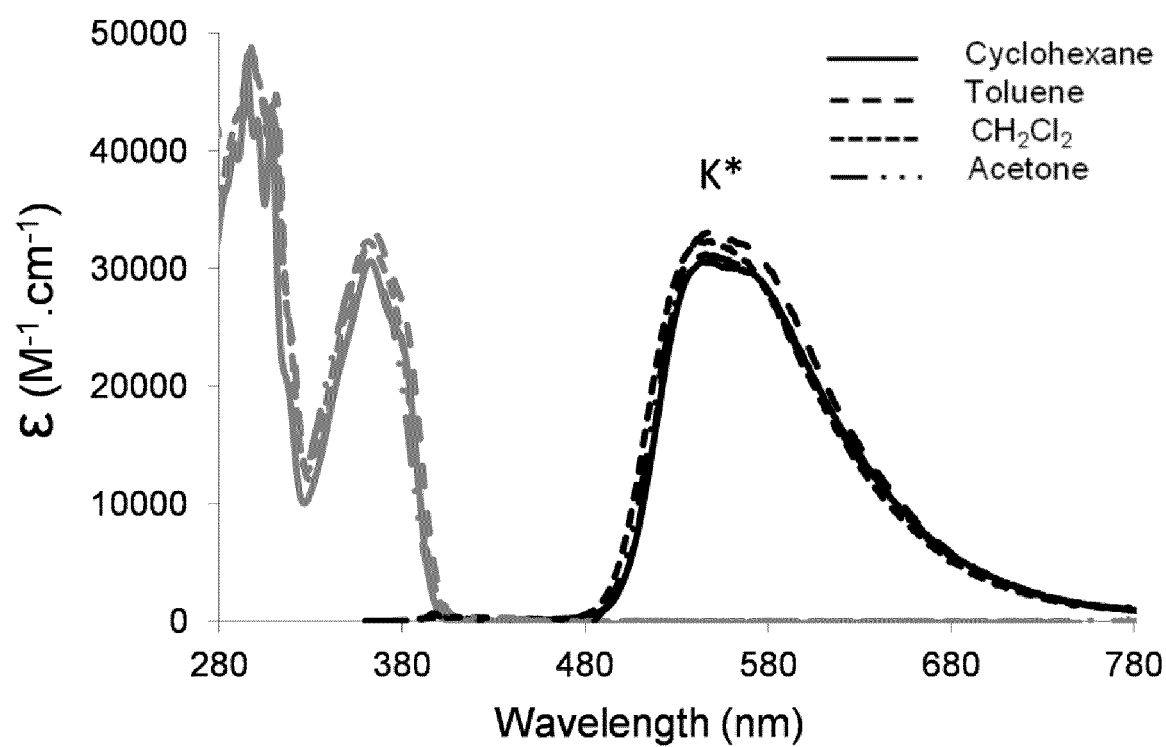
FIG. 2 corresponds to the absorption (in grey) and emission spectra (in black) in various solvents for comparative compound 6. Such data were recorded at room temperature (25° C.). Only K* band appears.
Figure 3:
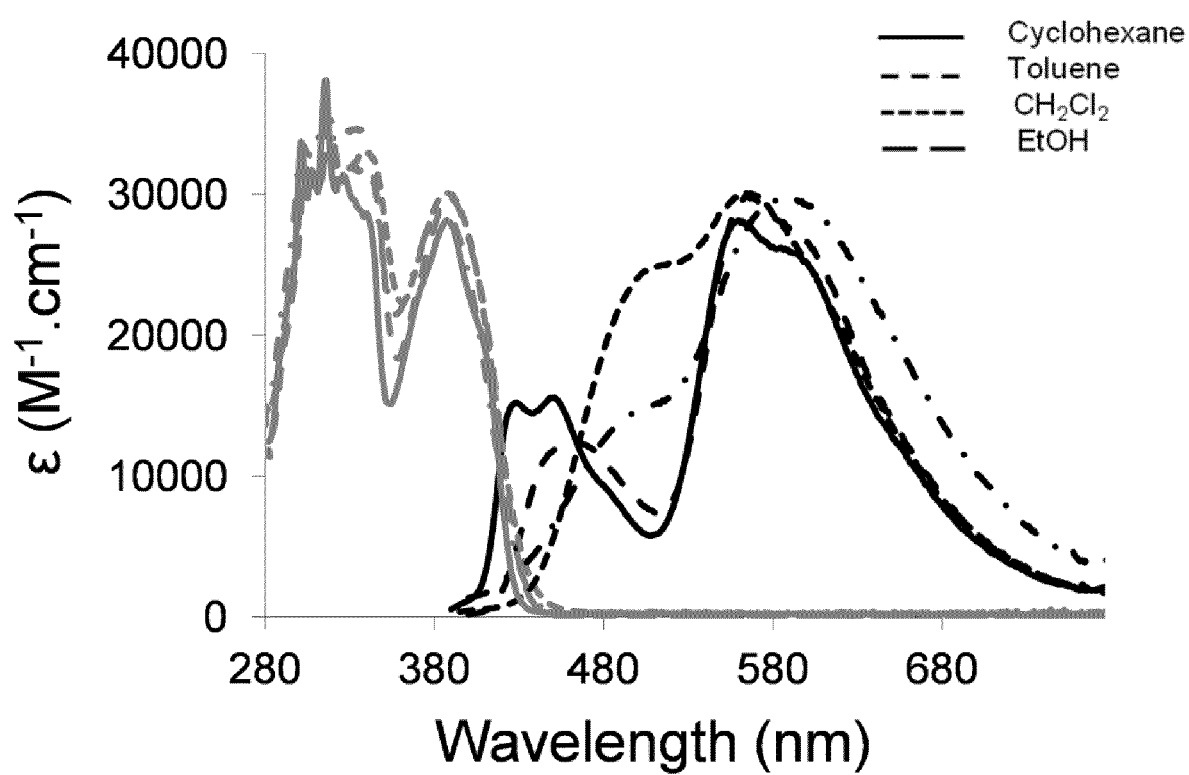
FIG. 3 corresponds to the absorption (in grey) and emission spectra (in black) in various solvents for compound 7. Such data were recorded at room temperature (25° C.).
Figure 4:
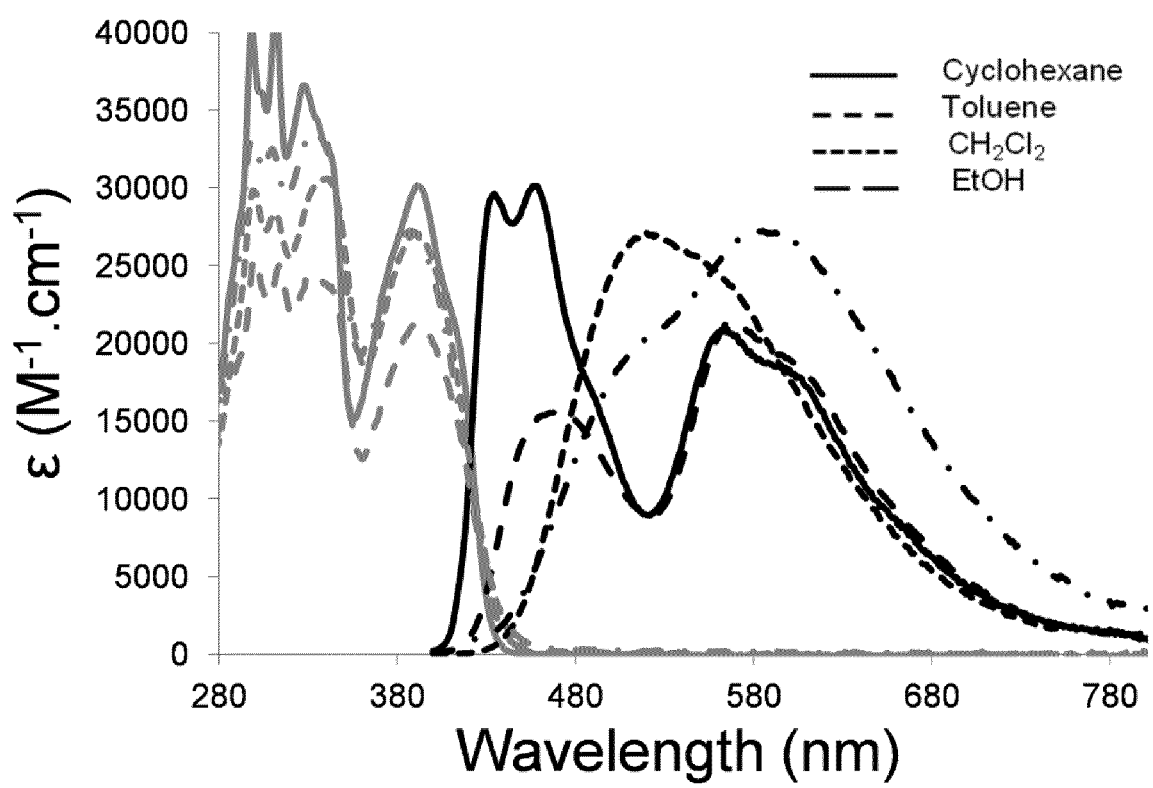
FIG. 4 corresponds to the absorption (in grey) and emission spectra (in black) in various solvents for compound 8. Such data were recorded at room temperature (25° C.).
Figure 5:
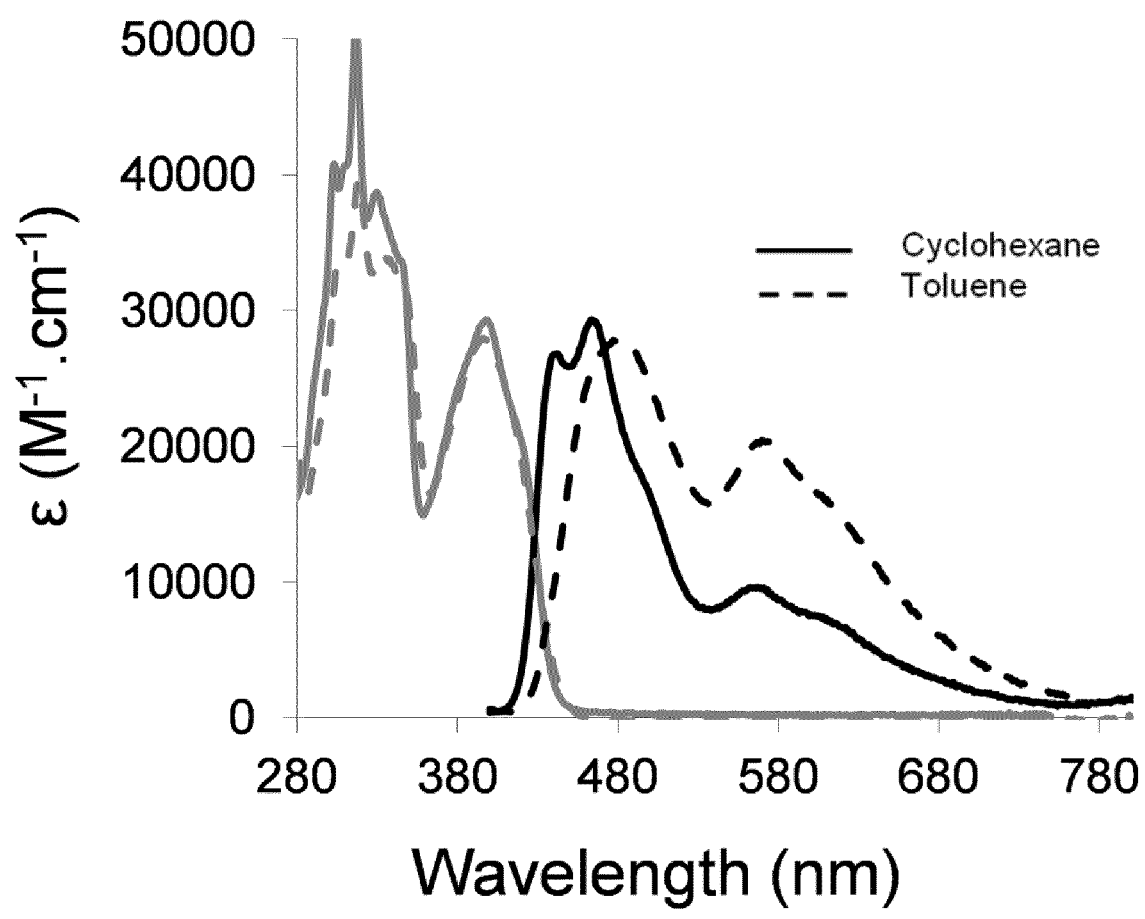
FIG. 5 corresponds to the absorption (in grey) and emission spectra (in black) in various solvents for compound 9. Such data were recorded at room temperature (25° C.).
Figure 6:
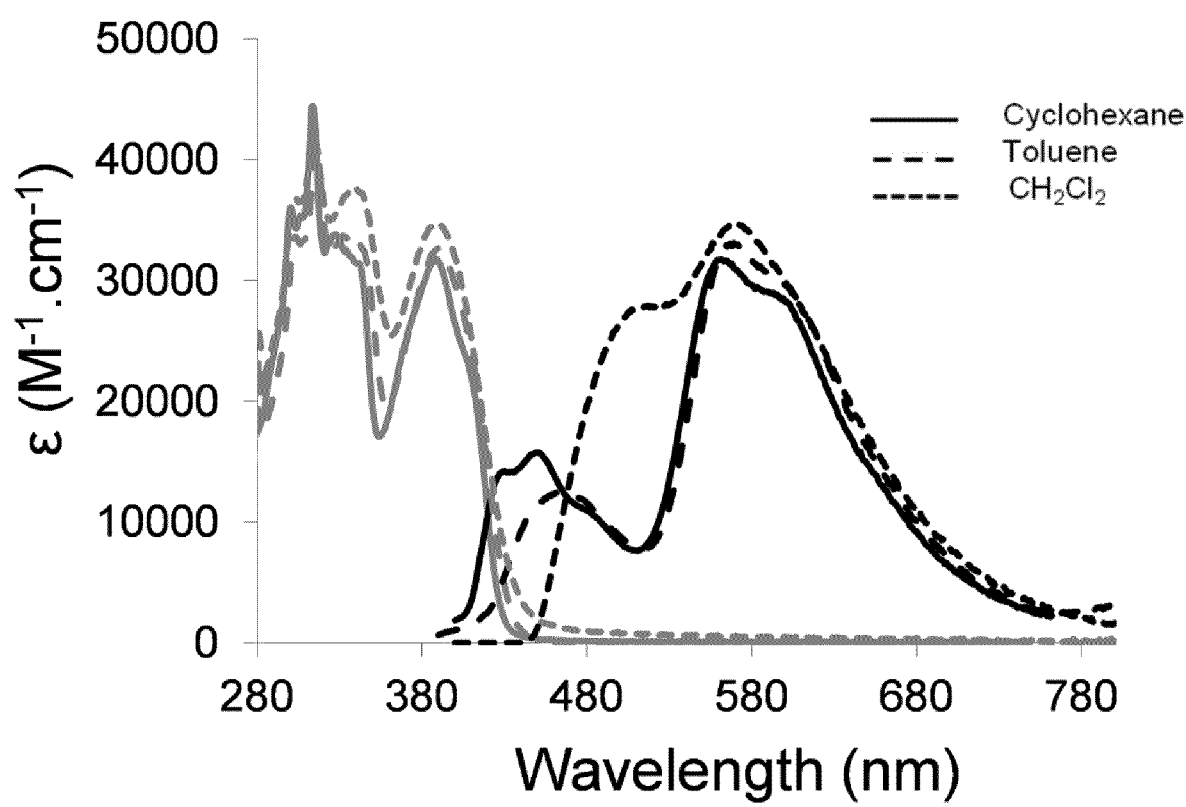
FIG. 6 corresponds to the absorption (in grey) and emission spectra (in black) in various solvents for compound 10. Such data were recorded at room temperature (25° C.).
Figure 7:
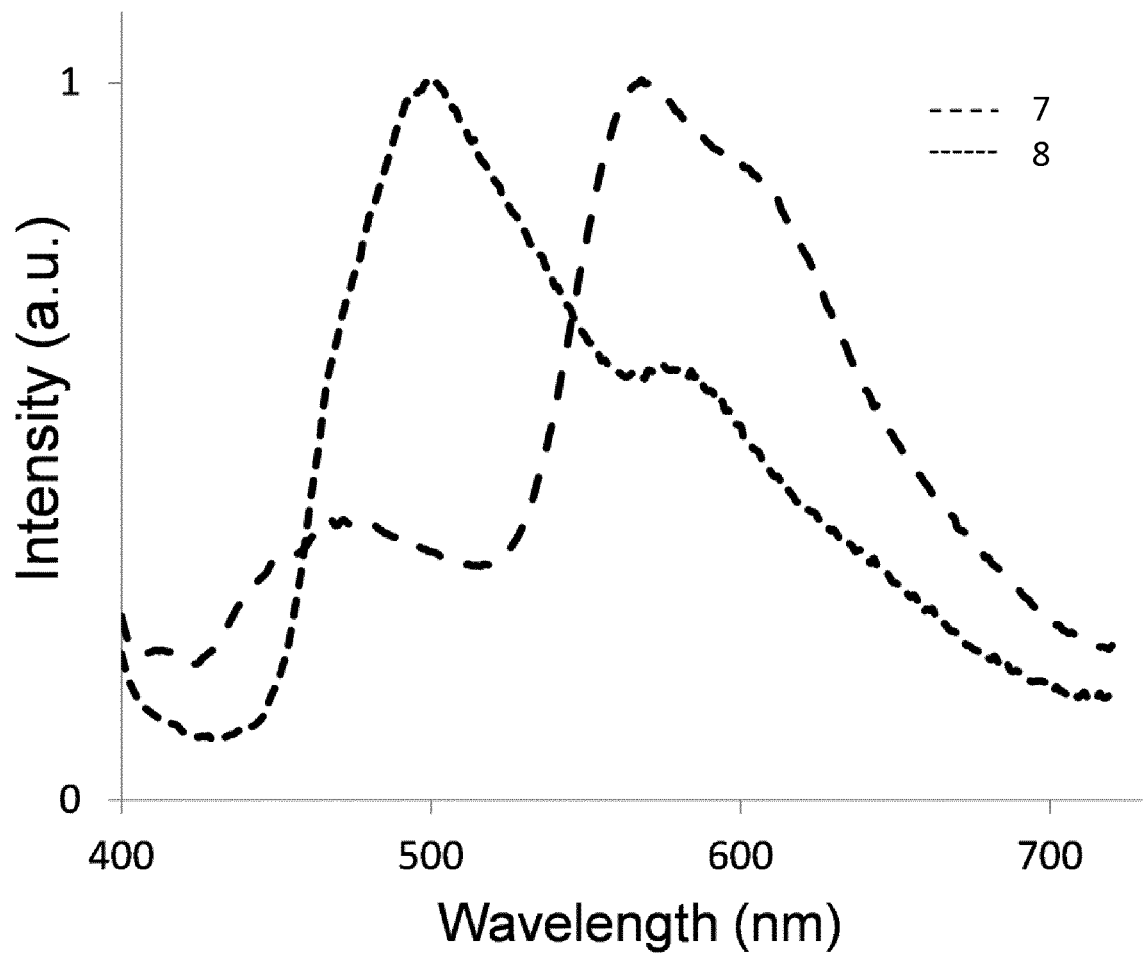
FIG. 7 corresponds to the solid-state emission spectra of compounds 7 and 8 in KBr pellets. Such data were recorded at room temperature (25° C.).
Figure 8:
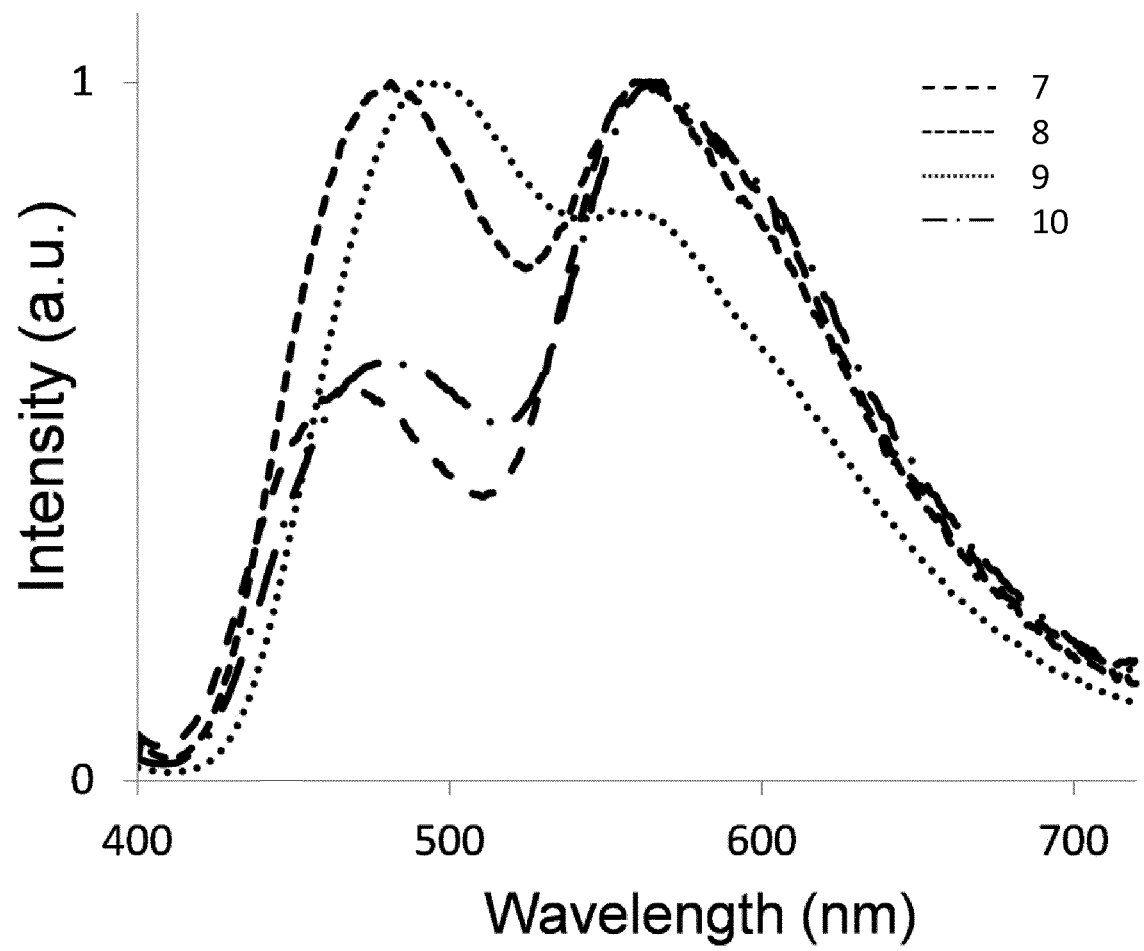
FIG. 8 corresponds to the solid-state emission spectra of compounds 7 to 10 PMMA/PS films. Such data were recorded at room temperature (25° C.) using an integration sphere.

The present invention concerns a compound of formula (I):

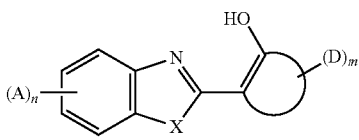

(I)

wherein:
A represents an electron-withdrawing group;
D represents an electron-donating group;
X is selected from the group consisting of: O, S and NR, wherein R is selected from the group consisting of: H, an alkyl group preferably comprising from 1 to 20 carbon atoms, an aryl group preferably comprising from 6 to 22 carbon atoms, and a heteroaryl group;
n is an integer from 1 to 4;
m is an integer from 1 to 6, preferably from 1 to 4;

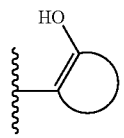 [SMILES: */C=C\O]

represents a condensed bicyclic aromatic radical comprising from 6 to 22 carbon atoms, and from 1 to 3 heteroatom(s) selected from the group consisting of: N, S and O;
the OH group being in ortho position of the condensed bicyclic aromatic radical relative to the

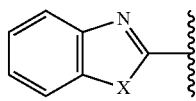

radical.

In one embodiment, in the compound of formula (I):

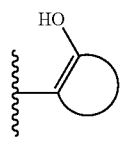 [SMILES: */C=C\O]

is not a quinoline, in particular is not:

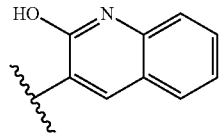

In one embodiment, the compound of formula (I) is not the following compound:

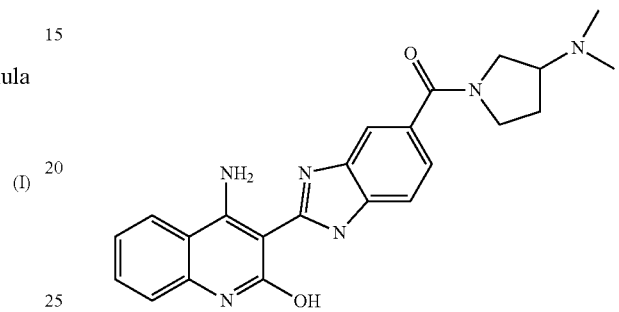

In one particular embodiment, in the formula (I) above-mentioned, X is O.

In one particular embodiment, in the formula (I) above-mentioned, X is NH.

In one particular embodiment, in the formula (I) above-mentioned, X is NR, wherein R is an alkyl group preferably comprising from 1 to 20 carbon atoms.

In one particular embodiment, in the formula (I) above-mentioned, X is NR, wherein R is an aryl group preferably comprising from 6 to 22 carbon atoms.

In one particular embodiment, in the formula (I) above-mentioned, X is NR, wherein R is a heteroaryl group preferably comprising from 6 to 22 atoms.

In one particular embodiment, in the formula (I) above-mentioned, X is S.

In one embodiment, in the formula (I) above-mentioned,

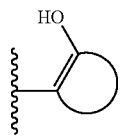

represents a condensed bicyclic aromatic radical comprising from 6 to 22 carbon atoms, preferably 8 carbon atoms, and 1 heteroatom selected from the group consisting of: N, S and O, preferably O.

In particular, in the formula (I) above-mentioned,

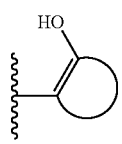 [SMILES: */C=C\O]

represents a condensed bicyclic aromatic radical comprising from 6 to 22 carbon atoms, preferably 8 carbon atoms, and 1 heteroatom selected from the group consisting of: S and O.

In particular,

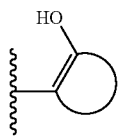 [SMILES: */C=C\O]

represents

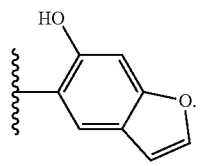

In one embodiment, in the formula (I) above-mentioned, n is 1 or 2.

In one embodiment, in the formula (I) above-mentioned, m is 1 or 2.

For sake of clarity, electron-withdrawing group A is not an alkyl group, such as for example tertio-butyl. Thus, compounds 9 and 10 disclosed in Massue et al., "Fluorescent 2-(2'-hydroxybenzofuran)benzoxazole borate complexes: synthesis, optical properties and theoretical calculations", Tetrahedron Letters, 2014, 55, 4136-41-40" do not fall within the compounds of formula (I) of the present invention.

In one embodiment, the electron-donating group D is selected from the group consisting of:

O$^-$;

OR$_a$, wherein R$_a$ is H or an alkyl group preferably comprising from 1 to 20 carbon atoms, in particular OMe;

NR$_b$R$_c$, wherein R$_b$ and R$_c$ are, independently of each other, selected from the group consisting of:

H;
alkyl group preferably comprising from 1 to 20 carbon atoms, preferably from 1 to 4 carbon atoms; and
aryl group preferably comprising from 6 to 22 carbon atoms, preferably a phenyl group;

NHC(O)R$_d$, wherein R$_d$ is selected from the group consisting of:

alkyl group preferably comprising from 1 to 20 carbon atoms preferably from 1 to 4 carbon atoms; and
aryl group preferably comprising from 6 to 22 carbon atoms, preferably a phenyl group;
an aryl group preferably comprising from 6 to 22 carbon atoms, preferably a phenyl group; and
an alkyl group preferably comprising from 1 to 20 carbon atoms;

said alkyl and aryl groups being optionally substituted with at least one electron-donating group, preferably selected from: O$^-$, OR$_a$, NR$_b$R$_c$ and —NHC(O)R$_d$, R$_a$, R$_b$, R$_c$ and R$_d$ being as defined according to the present invention.

In one embodiment, the electron-donating group D is selected from the group consisting of:

O$^-$;

OR$_a$, wherein R$_a$ is H or an alkyl group preferably comprising from 1 to 20 carbon atoms;

NHC(O)R$_d$, wherein R$_d$ is selected from the group consisting of:

alkyl group preferably comprising from 1 to 20 carbon atoms preferably from 1 to 4 carbon atoms; and
aryl group preferably comprising from 6 to 22 carbon atoms, preferably a phenyl group;
an aryl group preferably comprising from 6 to 22 carbon atoms, preferably a phenyl group; and
an alkyl group preferably comprising from 1 to 20 carbon atoms;

said alkyl and aryl groups being optionally substituted with at least one electron-donating group, preferably selected from: O, OR$_a$, NR$_b$R$_c$ and —NHC(O)R$_d$, R$_a$, R$_b$, R$_c$ and R$_d$ being as defined according to the present invention.

In one embodiment, the electron-donating group D comprises a π-electron conjugated chain comprising for example one or several alkynyl or alkenyl groups, the conjugation being possible by means of alternating alkenylene or alkynylene groups. Such π-electron conjugated chain allows the delocalization of π-electrons across all the adjacent aligned p-orbitals. The presence of such π-electron conjugated chain inside the group D does not change the electron-donating feature of said group D.

For example, an electron-donating group D comprising a π-electron conjugated chain may be:

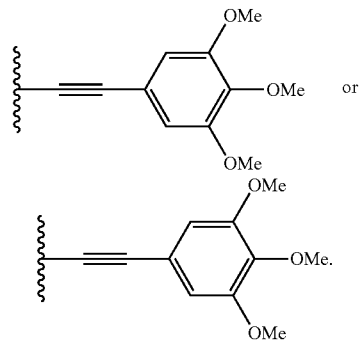

In one embodiment, the electron-donating group D is an aryl group comprising from 6 to 22 carbon atoms, preferably a phenyl group, optionally substituted with at least one electron-donating group preferably selected from: O$^-$, OR$_a$, NR$_b$R$_c$ and —NHC(O)R$_d$, R$_a$, R$_b$, R$_c$ and R$_d$ being as defined according to the present invention.

In one embodiment, the electron-donating group D has the following formula (A):

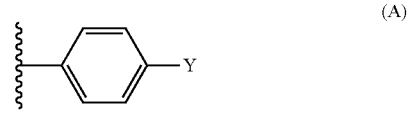

(A)

wherein Y is selected from: O$^-$, OR$_a$, NR$_b$R$_c$ and —NHC(O)R$_d$, R$_a$, R$_b$, R$_c$ and R$_d$ being as defined above.

In particular, the electron-donating group D is:

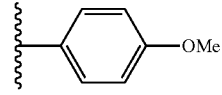 [SMILES: *c1ccc(OC)cc1]

In particular, the electron-donating group D is:

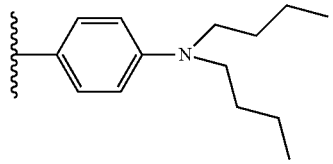 [SMILES: *c1ccc(N(CCCC)CCCC)cc1]

In one embodiment, the electron-donating group D has the following formula (B):

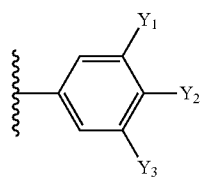

(B)

wherein $Y_1$, $Y_2$ and $Y_3$ represent, independently of each other, $OR_a$, $R_a$ being as defined above.

In particular, the electron-donating group D is:

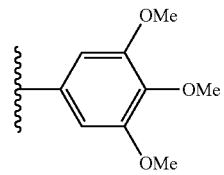 [SMILES: *c1cc(OC)c(OC)c(OC)c1]

In one embodiment, the electron-withdrawing group A is selected from the group consisting of:
halogen such as Br, Cl, F or I;
$C(O)R_e$, $R_e$ being selected from the group consisting of:
Cl;
H;
$OR_f$, $R_f$ being H or an alkyl group preferably comprising from 1 to 20 carbon atoms; and
an alkyl group preferably comprising from 1 to 20 carbon atoms;
$NO_2$;
$SO_2NR_gR_h$, $R_g$ and $R_h$ representing, independently of each other, an alkyl group preferably comprising from 1 to 20 carbon atoms or an aryl group preferably comprising from 6 to 22 carbon atoms;
CN;
$CF_3$;
alkyl group, preferably comprising from 1 to 20 carbon atoms, substituted with at least one group selected from: halogen such as F, $NO_2$, CN, $C(O)R_e$, $SO_2NR_gR_h$ and $CF_3$, wherein $R_e$, $R_g$ and $R_h$ are as defined above, said alkyl being optionally substituted with a heteroaryl, said heteroaryl being optionally substituted with a substituted heteroaryl;
aryl group, preferably comprising from 6 to 22 carbon atoms, substituted with at least one group selected from: halogen such as F, $NO_2$, CN, $C(O)R_e$, $SO_2NR_gR_h$ and $CF_3$, wherein $R_e$, $R_g$ and $R_h$ are as defined above;
—$S(O)_2$—W, W being a heteroaryl being optionally substituted with a substituted heteroaryl;
$SO_3H$;

a radical having the following formula:

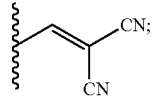 [SMILES: *C=C(C#N)C#N]

and
$N^+R_iR_jR_k$, wherein $R_i$, $R_j$, $R_k$, and $R_l$, are, independently of each other, H or an alkyl group preferably comprising from 1 to 20 carbon atoms, said alkyl group being optionally substituted with at least one group selected from: halogen such as F, $NO_2$, CN, $C(O)R_e$, $SO_2NR_gR_h$ and $CF_3$, wherein $R_e$, $R_g$ and $R_h$ are as defined above.

In one embodiment, the electron-withdrawing group A is selected from the group consisting of:
halogen such as Br, Cl, F or I;
$C(O)R_e$, $R_e$ being selected from the group consisting of:
Cl;
H;
$OR_g$, $R_f$ being H or an alkyl group preferably comprising from 1 to 20 carbon atoms; and
an alkyl group preferably comprising from 1 to 20 carbon atoms;
$NO_2$;
$SO_2NR_gR_h$, $R_g$ and $R_h$ representing, independently of each other, an alkyl group preferably comprising from 1 to 20 carbon atoms or an aryl group preferably comprising from 6 to 22 carbon atoms;
CN;
$CF_3$;
alkyl group, preferably comprising from 1 to 20 carbon atoms, substituted with at least one group selected from: halogen such as F, $NO_2$, CN, $C(O)R_e$, $SO_2NR_gR_h$ and $CF_3$, wherein $R_e$, $R_g$ and $R_h$ are as defined above;
aryl group, preferably comprising from 6 to 22 carbon atoms, substituted with at least one group selected from: halogen such as F, $NO_2$, CN, $C(O)R_e$, $SO_2NR_gR_h$ and $CF_3$, wherein $R_e$, $R_g$ and $R_h$ are as defined above;
$SO_3H$; and
$N^+R_iR_jR_kR_l$, wherein $R_i$, $R_k$, and $R_j$ are, independently of each other, H or an alkyl group preferably comprising from 1 to 20 carbon atoms, said alkyl group being optionally substituted with at least one group selected from: halogen such as F, $NO_2$, CN, $C(O)R_e$, $SO_2NR_gR_h$ and $CF_3$, wherein $R_e$, $R_g$ and $R_h$ are as defined above.

In one embodiment, the electron-withdrawing group A comprises a π-electron conjugated chain comprising for example one or several alkynyl or alkenyl groups, the conjugation being possible by means of alternating alkenylene or alkynylene groups. Such π-electron conjugated chain allows the delocalization of π-electrons across all the adjacent aligned p-orbitals. The presence of such π-electron conjugated chain inside the group A does not change the electron-withdrawing feature of said group A.

For example, an electron-withdrawing group A comprising a π-electron conjugated chain may be:

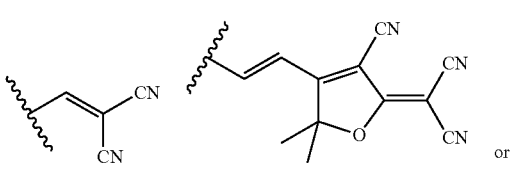

or

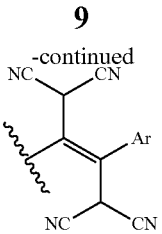

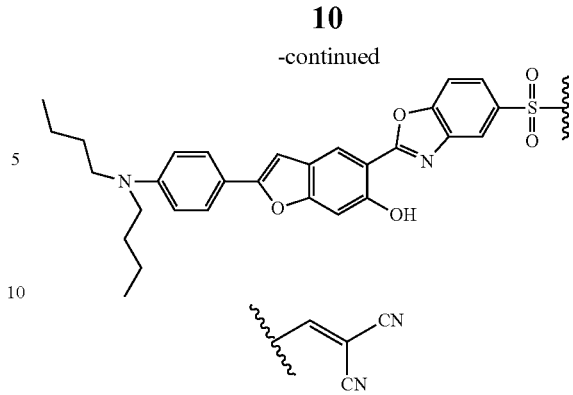

In one embodiment, the electron-withdrawing group A is —C(O)H.

In one embodiment, the electron-withdrawing group A is —C(O)OH.

In one embodiment, the electron-withdrawing group A is —C(O)Cl.

In one embodiment, the electron-withdrawing group A is $NO_2$.

In one embodiment, the electron-withdrawing group A is $NH_4^+$.

In one embodiment, the electron-withdrawing group A is an aryl group comprising from 6 to 22 carbon atoms substituted with at least one nitro group, preferably a phenyl group substituted with at least one nitro group.

In one embodiment, the electron-withdrawing group A is an aryl group comprising from 6 to 22 carbon atoms substituted with at least one fluorine atom, preferably a phenyl group substituted with at least one fluorine atom.

In one particular embodiment, the electron-withdrawing group A is CN.

In one particular embodiment, the electron-withdrawing group A is $CF_3$.

In one particular embodiment, the electron-withdrawing group A is —C(O)OMe.

In one particular embodiment, the electron-withdrawing group A is F.

In one particular embodiment, the electron-withdrawing group A is Br.

In one embodiment, the electron-withdrawing group A is selected from the group consisting of the following radicals:

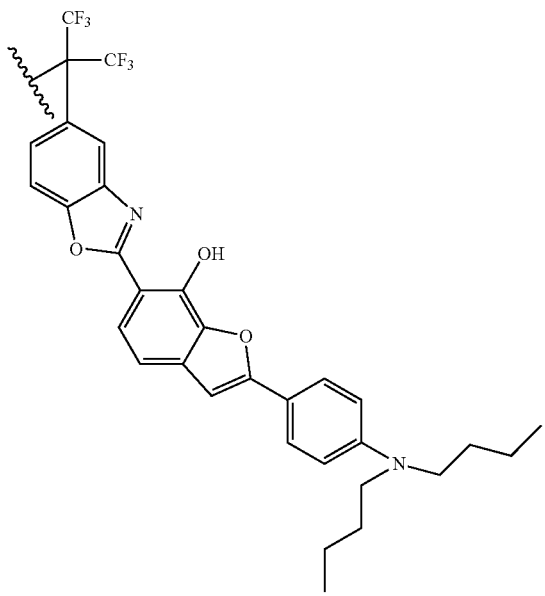

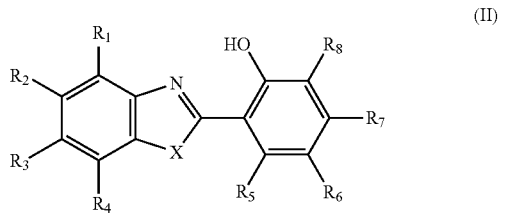

The present invention also relates to a compound of formula (II):

$$\text{(II)}$$

wherein:

$R_1$, $R_2$, $R_3$ and $R_4$ represent, independently of each other, H or an electron-withdrawing group A;

$R_5$, $R_6$, $R_7$ and $R_8$ represent, independently of each other, H or an electron-donating group D;

or $R_5$ and $R_6$ form, together with the carbon atoms carrying them, an at least partially unsaturated cycle comprising from 4 to 6 atoms, preferably 5 atoms, said cycle comprising at least one heteroatom selected from the group consisting of: N, O and S, and said cycle being optionally substituted by at least one electron-donating group D;

or $R_6$ and $R_7$ form, together with the carbon atoms carrying them, an at least partially unsaturated cycle comprising from 4 to 6 atoms, preferably 5 atoms, said cycle comprising at least one heteroatom selected from the group consisting of: N, O and S, and said being optionally substituted by at least one electron-donating group D; or $R_7$ and $R_8$ form, together with the carbon atoms carrying them, an at least partially unsaturated cycle comprising from 4 to 6 atoms, preferably 5 atoms, said cycle comprising at least one heteroatom selected from the group consisting of: N, O and S, and said being optionally substituted by at least one electron-donating group D;

X, A and D being as defined according to the present invention;

at least one of $R_5$ and $R_6$, or $R_6$ and $R_7$, or $R_7$ and $R_8$, form said at least partially unsaturated cycle;

at least one of $R_1$, $R_2$, $R_3$ and $R_4$ is an electron-withdrawing group A; and said compound of formula (II) comprising at least one electron-donating group D.

In one embodiment, in the formula (II) above-mentioned, X is O.

In one embodiment, in the formula (II) above-mentioned, X is NH.

In one particular embodiment, in the formula (II) above-mentioned, X is NR, wherein R is an alkyl group preferably comprising from 1 to 20 carbon atoms.

In one particular embodiment, in the formula (II) above-mentioned, X is NR, wherein R is an aryl group preferably comprising from 6 to 22 carbon atoms.

In one particular embodiment, in the formula (II) above-mentioned, X is NR, wherein R is a heteroaryl group.

In one embodiment, in the formula (II) above-mentioned, X is S.

In one embodiment, in the formula (II) above-mentioned, $R_2$ is an electron-withdrawing group A.

In one embodiment, in the formula (II) above-mentioned, $R_1$, $R_3$ and $R_4$ are H.

In one embodiment, in the formula (II) above-mentioned, $R_1$ is an electron-withdrawing group A.

In one embodiment, in the formula (II) above-mentioned, $R_4$ is Br.

In one embodiment, in the formula (II) above-mentioned, $R_5$ and $R_8$ are H.

n one embodiment, in the formula (II) above-mentioned, $R_5$ and $R_6$ form, together with the carbon atoms carrying them, an at least partially unsaturated cycle comprising from 4 to 6 atoms, preferably 5 atoms, said cycle comprising at least one heteroatom selected from the group consisting of: N, O and S, and said being optionally substituted by at least one electron-donating group D. In particular, $R_5$ and $R_6$ form, together with the carbon atoms carrying them, an at least partially unsaturated cycle comprising 5 atoms, said cycle comprising one oxygen atom and being substituted with one electron-donating group D.

In one embodiment, in the formula (II) above-mentioned, $R_7$ and $R_8$ form, together with the carbon atoms carrying them, an at least partially unsaturated cycle comprising from 4 to 6 atoms, preferably 5 atoms, said cycle comprising at least one heteroatom selected from the group consisting of: N, O and S, and said being optionally substituted by at least one electron-donating group D. In particular, $R_7$ and $R_8$ form, together with the carbon atoms carrying them, an at least partially unsaturated cycle comprising 5 atoms, said cycle comprising one oxygen atom and being substituted with one electron-donating group D.

In one embodiment, in the formula (II) above-mentioned, $R_6$ and $R_7$ form, together with the carbon atoms carrying them, an at least partially unsaturated cycle comprising from 4 to 6 atoms, preferably 5 atoms, said cycle comprising at least one heteroatom selected from the group consisting of: N, O and S, and said being optionally substituted by at least one electron-donating group D. In particular, $R_6$ and $R_7$ form, together with the carbon atoms carrying them, an at least partially unsaturated cycle comprising 5 atoms, said cycle comprising one oxygen atom and being substituted with one electron-donating group D.

The present invention also relates to a compound having the following formula (III):

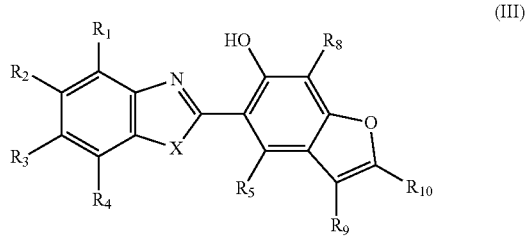

(III)

wherein:

$R_9$ and $R_{10}$ represent, independently of each other, H or an electron-donating group D;

$R_1$, $R_2$, $R_3$, $R_4$, $R_5$, $R_8$, X and D being as defined according to the present invention.

The compound of formula (III) corresponds notably to a compound of formula (II) wherein $R_6$ and $R_7$ form, together with the carbon atoms carrying them, a furan substituted with $R_9$ and $R_{10}$.

In one embodiment, in the formula (III) above-mentioned, X is O.

In one embodiment, in the formula (III) above-mentioned, X is NH.

In one particular embodiment, in the formula (I) above-mentioned, X is NR, wherein R is an alkyl group preferably comprising from 1 to 20 carbon atoms.

In one particular embodiment, in the formula (I) above-mentioned, X is NR, wherein R is an aryl group preferably comprising from 6 to 22 carbon atoms.

In one particular embodiment, in the formula (I) above-mentioned, X is NR, wherein R is a heteroaryl group.

In one embodiment, in the formula (III) above-mentioned, X is S.

In one embodiment, in the formula (III) above-mentioned, $R_2$ is an electron-withdrawing group A.

In one embodiment, in the formula (III) above-mentioned, $R_1$ is an electron-withdrawing group A.

In one embodiment, in the formula (III) above-mentioned, $R_4$ is Br.

In one embodiment, in the formula (III) above-mentioned, $R_1$, $R_3$ and $R_4$ are H.

In one embodiment, in the formula (III) above-mentioned, $R_5$ and $R_8$ are H.

In one embodiment, in the formula (III) above-mentioned, $R_9$ is H.

In one embodiment, in the formula (III) above-mentioned, $R_{10}$ is an electron-donating group D as defined according to the invention.

In one embodiment, the compound of formula (III) corresponds to a compound of formula (III-a) having the following formula:

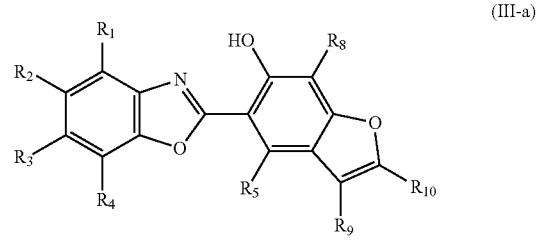

(III-a)

$R_1$, $R_2$, $R_3$, $R_4$, $R_5$, $R_8$, $R_9$, $R_{10}$ and D being as defined according to the invention.

The present invention also relates to a compound having the following formula (IV):

(IV)

wherein:
R₁₁ represents H or an electron-donating group D;
R₁, R₂, R₃, R₄, R₅, R₈, X and D being as defined according to the invention.

The compound of formula (IV) corresponds notably to a compound of formula (III) wherein R₉ is H, and R₁₀ is

[structure showing phenyl group with R₁₁ substituent]

In one embodiment, in the formula (IV) above-mentioned, X is O.

In one embodiment, in the formula (IV) above-mentioned, X is NH.

In one particular embodiment, in the formula (IV) above-mentioned, X is NR, wherein R is an alkyl group preferably comprising from 1 to 20 carbon atoms.

In one particular embodiment, in the formula (IV) above-mentioned, X is NR, wherein R is an aryl group preferably comprising from 6 to 22 carbon atoms.

In one particular embodiment, in the formula (IV) above-mentioned, X is NR, wherein R is a heteroaryl group.

In one embodiment, in the formula (IV) above-mentioned, X is S.

In one embodiment, in the formula (IV) above-mentioned, R₂ is an electron-withdrawing group A as defined according to the invention.

In one embodiment, in the formula (IV) above-mentioned, R₁, R₃ and R₄ are H.

In one embodiment, in the formula (IV) above-mentioned, R₅ and R₈ are H.

In one embodiment, in the formula (IV) above-mentioned, R₁₁ is an electron-donating group D as defined according to the invention.

The present invention also relates to a compound having the following formula (V):

(V)

wherein:
R' and R" represent, independently of each other, H or an alkyl group preferably comprising from 1 to 20 carbon atoms;
R₃, R₅, R₈ and X being as defined according to the invention.

The present invention also relates to a compound having the following formula (IV-bis):

(IV-bis)

wherein:
R₁₂, R₁₃ and R₁₄, independently of each other, represents an electron-donating group D;
R₁, R₂, R₃, R₄, R₅, R₈, X and D being as defined according to the invention.

The present invention also relates to a compound having the following formula (IV-bis-1):

(IV-bis)

wherein R₁, R₂, R₃, R₄, R₅, R₈, X and D being as defined according to the invention.

In one embodiment, among the compounds of formulae (I), (II), (III), (IV), (IV-bis), (IV-bis-1) and (V), mention may be made to the following ones:

15 16
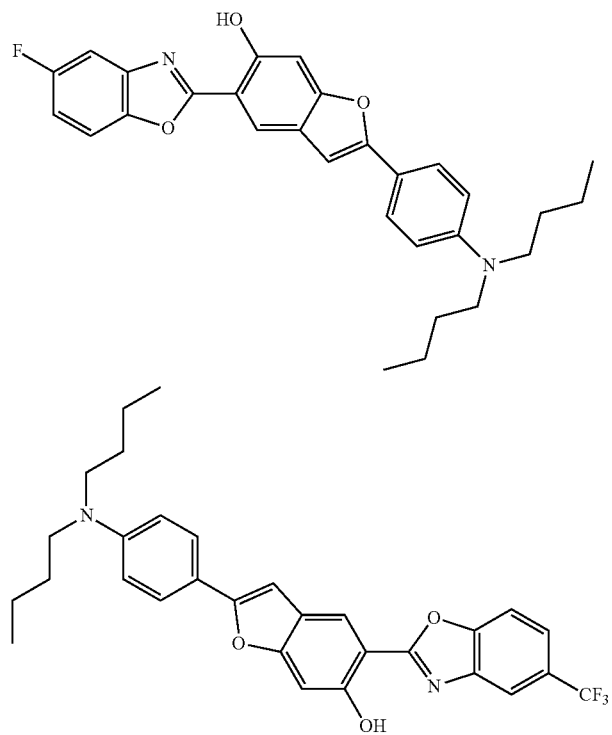
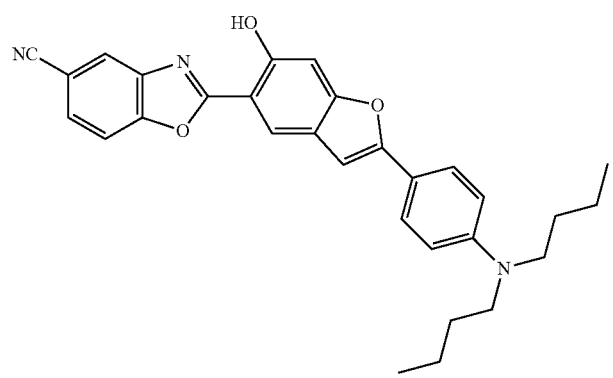
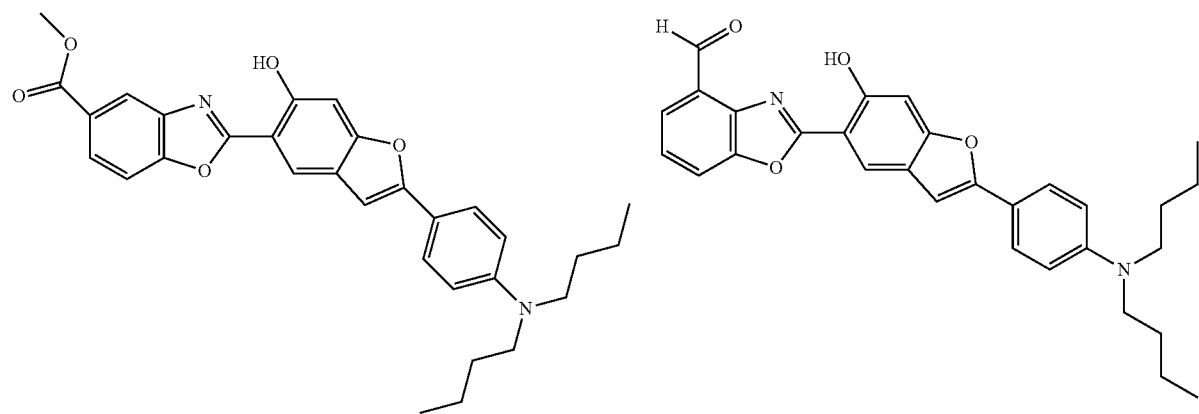

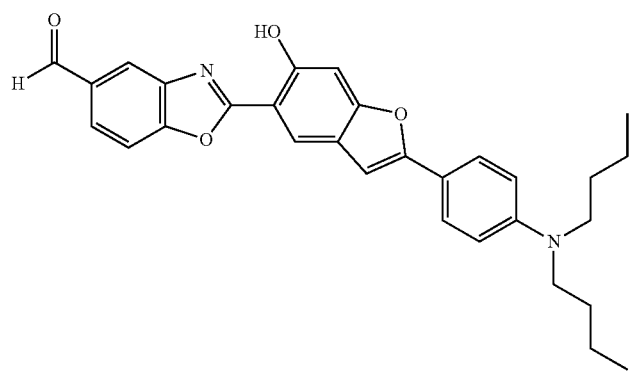
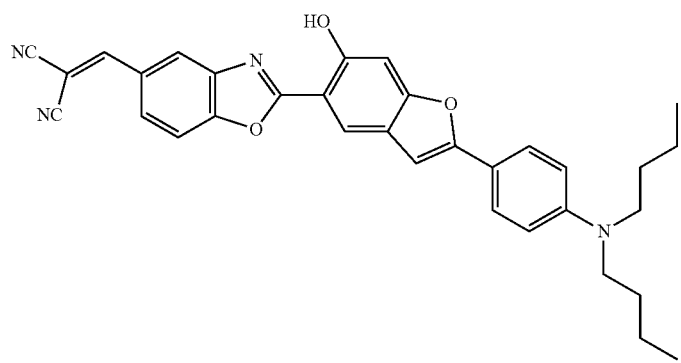
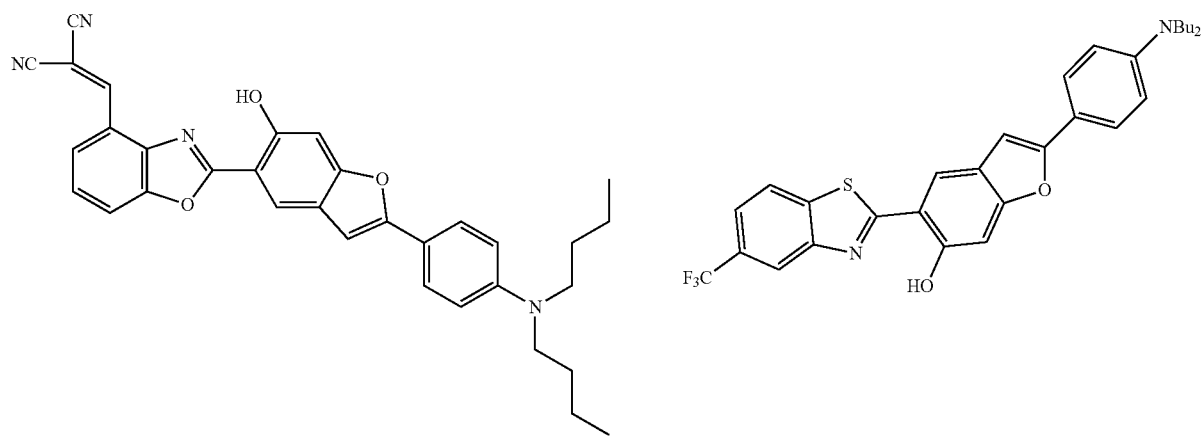

-continued

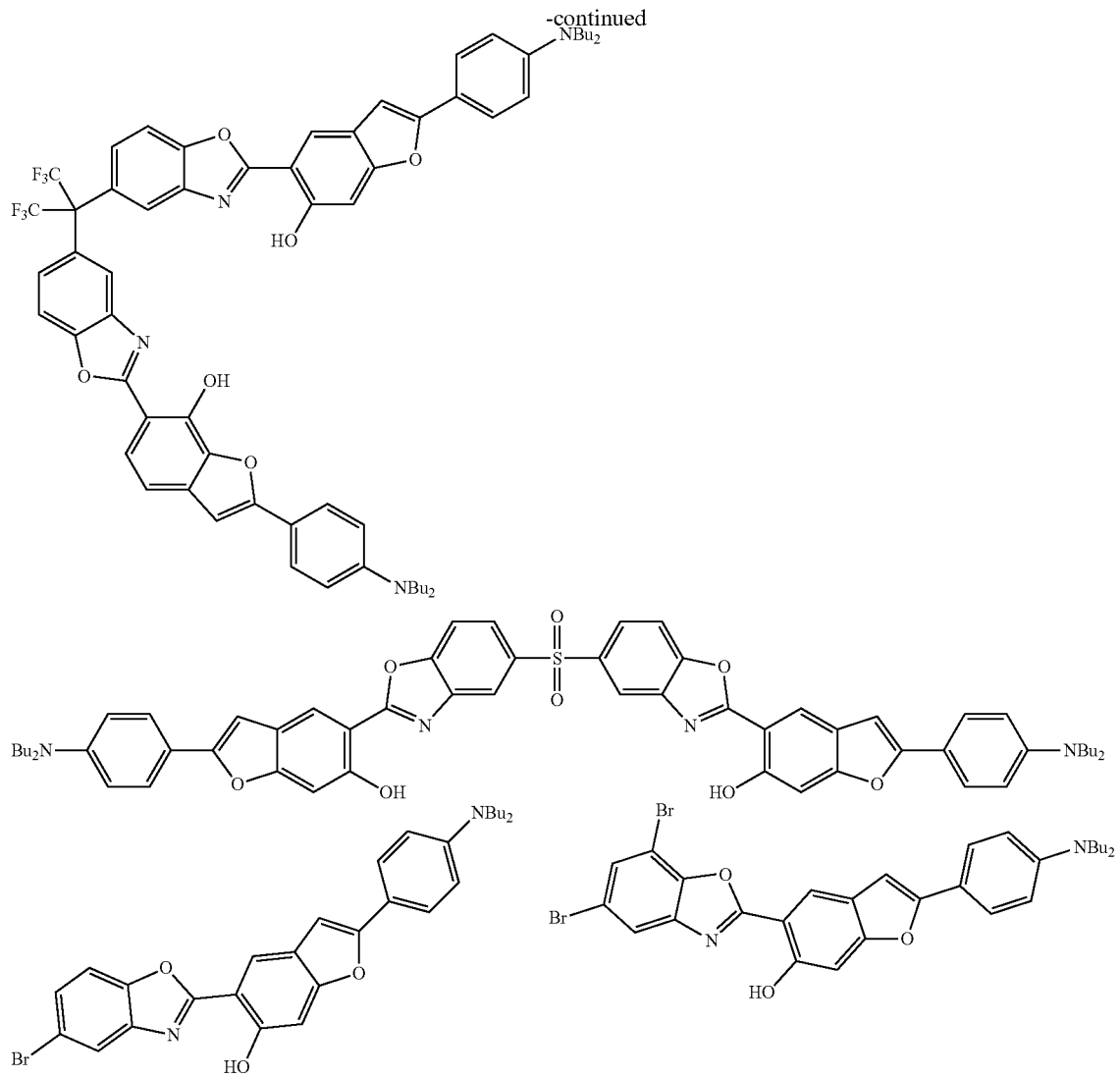

The present invention also relates to the process of preparation of a compound of formula (I) above-mentioned, said process comprising reacting a compound of formula (VI):

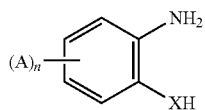
(VI)

with a compound of formula (VII):

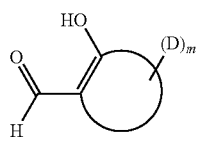
(VII)

wherein

A, X, D, n and m are as defined according to the invention.

In one embodiment, the reaction between the compound of formula (VI) and the compound of formula (VII) is carried out in presence of a base, KCN, and a boronic acid, such as for example PhB(OH)$_2$. In a particular embodiment, the reaction is carried out in a polar solvent, such as for example methanol, preferably at room temperature (about 25° C.), notably under atmospheric pressure.

In another embodiment, the reaction between the compound of formula (VI) and the compound of formula (VII) is carried out in a polar solvent, such as for example ethanol, under reflux. Then, 2,3-dichloro-5,6-dicyano-1,4-benzoquinone is added to the reaction mixture, and the reaction medium was mixed at room temperature (about 25° C.).

In one embodiment, in the process above-mentioned, the compound of formula (VI) is a compound of formula (VI-a):

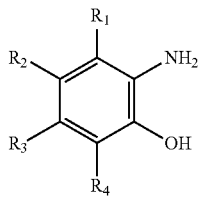

(VI-a)

and the compound of formula (VII) is a compound of formula (VII-a):

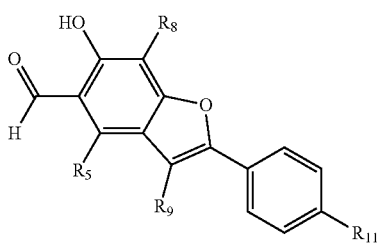

(VII-a)

wherein $R_1$, $R_2$, $R_3$, $R_4$, $R_5$, $R_8$, $R_9$, $R_{11}$ are as defined according to the invention.

In one embodiment, the compound of formula (VII-a) results from the reaction of a compound of formula (VIII-a):

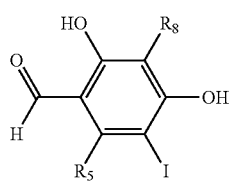

(VIII-a)

with a compound of formula (IX-a):

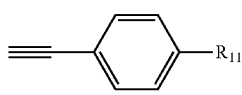

(IX-a)

wherein $R_5$, $R_8$ and $R_{11}$ are as defined above, via a Sonogashira cross-coupling, preferably carried out in presence of CuI, $PdCl_2(PPh_3)_2$ and a base.

[Definitions]

As used herein, the term "condensed bicyclic aromatic radical" means a radical having two aromatic rings which are fused to each other. Examples of such radical are benzofuran, benzothiophene, indene, purine, isoquinoline, quinoline, indole, napthalene. In particular, the condensed bicyclic aromatic radical is benzofuran.

The charge distribution in a molecule is typically discussed with respect to two interacting effects:
an inductive effect, which is a function of the electronegativity differences that exist between atoms (and groups); and a resonance effect, in which electrons move in a discontinuous fashion between parts of a molecule.

Typically, the strength of donor/acceptor couple can be determined by ab initio calculation of density difference between excited state and fundamental state. The common way to define the EDG (electron-donating group) or EWG (electron-withdrawing group) character of a function is to use the couple between the function and the hydrogen (H). The CT (charge transfer) is determined as the distance separating the barycenters of density depletion and gain following the electronic transitions. This CT distance will be correlated to the relative stability of the two tautomeric forms computed as relative free energies.

As used herein, the term "electron-withdrawing group" is also called "electron acceptor" which has its electronic density rising by going from the fundamental state to the excited state. Such term denotes the tendency of a substituent to attract valence electrons from neighboring atoms or atoms on the pi-delocalized system, i.e., the substituent is electronegative with respect to neighboring atoms or atoms on the pi-delocalized system.

As used herein, the term "electron-donating group" is also called "electron donor" which has its electronic density decreasing by going from the fundamental state to the excited state. Such term denotes the tendency of a substituent to provide valence electrons to neighboring atoms or atoms on the π-delocalized system, i.e., the substituent is electropositive with respect to neighboring atoms.

As used herein, the term "alkyl" means a saturated aliphatic hydrocarbon group which may be straight or branched having preferably from 1 to 20 carbon atoms in the chain, optionally comprising at least one unsaturation. Preferred alkyl groups have 1 to 12 carbon atoms in the chain. For example, the alkyl group is a methyl, a propyl, a butyl, a tertiobutyl, a pentyl or an isopropyl. Such alkyl group may include substituents. Said alkyl can also be a cyclic alkyl.

As used herein, the term "aryl" refers to an aromatic monocyclic or bicyclic hydrocarbon ring system having preferably 6 to 22 carbons, more preferably from 6 to 10 carbon atoms. Examples of aryl moieties include, but are not limited to, phenyl, naphthyl, and anthracenyl. In case of electron-attracting group, substituents are preferably selected from the group consisting of those defined previously for group A. In case of electron-donating group, substituents are preferably selected from the group consisting of those defined previously for group D.

As used herein, the term "heteroaryl" refers to an aromatic 5 to 8 membered monocyclic, 8 to 12 membered bicyclic, having 1 to 3 heteroatoms if monocyclic, 1 to 6 heteroatoms if bicyclic, said heteroatoms being selected from O, N, or S. Examples of heteroaryl groups are thiophene, pyridine, furan, pyrolle, benzofuran, benzooxazole.

As used herein, the term "substituents" refers to a group "substituted" on an alkyl, aryl, or heteroaryl group at any atom of that group. Suitable substituents include, without limitation, alkyl, alkenyl, alkynyl, alkoxy, halo, ester, hydroxy, cyano, nitro, amino, dialkylamino, $SO_3H$, perfluoroalkyl, perfluoroalkoxy, amido, sulfonamido, aryl, heteroaryl, heterocyclyl, and cycloalkyl. The preferred substituents on alkyl, aryl or heteroaryl groups are OH, amino, dialkylamino, alkoxy, halo, perfluoroalkyl such as $CF_3$ and hereoaryl.

As used herein, the term "alkylene" means a divalent saturated aliphatic hydrocarbon radical, which may be linear or branched, preferably having from 1 to 24 carbon atoms in the chain.

As used herein, the term "alkenylene" means a divalent linear or branched hydrocarbon radical, preferably having 2 to 6 carbon atoms and having at least one double bond, and includes for example ethenylene.

As used herein, the term "alkynylene" means a divalent linear or branched hydrocarbon radical, preferably having 2 to 6 carbon atoms and having at least one triple bond. Preferred alkynylene groups include ethynylene (—C≡C—).

As used herein, the term "an at least partially unsaturated cycle" means that the cycle is partially unsaturated or fully unsaturated. Example of fully unsaturated cycle is phenyl. Examples of at least partially unsaturated cycle are furan, thiophene, pyrrole, phenyl, thiazole, imidazole, preferably said cycle being furan. Such aryl group may include substituents.

As used herein, the compounds of formula (I), (II), (III), (IV) or (V) are also called "emitters" or even "organic emitters".

As used herein, the term "dual emission" means that upon photoexcitation, for example at $\lambda_{ex}$ (excitation wavelength) a compound will emit two distinct emission band $\lambda_{emE}$ and $\lambda_{emK}$ corresponding respectively to E* and K* states.

As used herein, the term "E*" means the enol at its excited state of the compounds according to the invention, having notably the following formula:

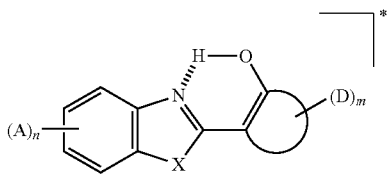

As used herein, the term "K*" means the keto at its excited state of the compounds according to the invention, having notably the following formula:

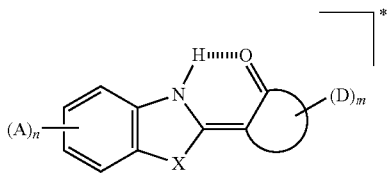

As used herein, the term "fluorophore", also called "fluorochrome" or "chromophore", is a fluorescent chemical compound that can re-emit light upon light excitation.

As used herein, the term "protic solvent" means a solvent that include at least one hydrogen atom that is capable of being released in the form of a proton.

As used herein, the term "aprotic solvent" means a solvent that is considered as not being protic. In particular, such solvents are not suitable for releasing a proton or for accepting one. Examples of aprotic solvent are toluene, dimethylformamide, acetone, dimethyl sulfoxide.

As used herein, the term "compound according to the invention", or "compound of the invention" corresponds to a compound of formulae (I), (II), (III), (IV), (V) or their mixtures thereof.

As used herein, the term "transparent" typically means that a person may read alphanumeric characters even the film is placed between said person and said alphanumeric characters.

Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

As used herein, the term "dielectric constant of a solvent" is a measure of its polarity. The higher the dielectric constant of a solvent, the more polar it is.

As used herein, the term "conductive polymer" means organic polymers that are able to transport charges (electrons and holes).

As used herein, the term "organic semiconductor polymer" means a polymer of an organic compound capable of exhibiting the properties of a semiconductor.

[Uses]

The present invention also relates to a solution comprising at least one compound according to the invention, and a solvent.

Preferably, the solvent is selected from the group consisting of: solvents with low dielectric constant and solvents with high dielectric constant.

In particular, solvents with low dielectric constant are selected from the group consisting of: toluene, cyclohexane, dichloromethane and mixtures thereof.

In particular, solvents with high dielectric constant are selected from the group consisting of: alcohols, dimethylsulphoxide, water, acetone, acetonitrile and mixtures thereof.

The present invention also relates to a solid material (S) comprising, or consisting of, at least one compound according to the invention.

In one embodiment, the solid material (S) consists of at least one compound according to the invention. In this case, the at least one compound according to the invention is in a solid state, such as for example in powder form.

In one specific embodiment, said solid material or compound according to the invention is a crystal, for example a monocrystal.

In one embodiment, the solid material further comprises an inorganic solid for example selected from the group consisting of: KBr matrix pellets, alumine, silica, zeolithe, clays, titanium oxyde and titanium silicium. In particular, the at least one compound according to the invention is combined with or introduced into said inorganic solid.

In particular, the at least one compound according to the invention is dispersed as a solid powder into KBr matrix pellets.

The invention also relates to a material (M) comprising at least one compound according to the invention, and at least one polymer and/or polymeric material and/or an organic matrix, said organic matrix may optionally comprise an inorganic material such as dopants. In one embodiment, the compound(s) according to the invention is(are) encapsulated in said polymer and/or polymeric material and/or organic matrix.

In one embodiment, the material (M) comprises at least one compound according to the invention, and at least one organic matrix.

In one embodiment, the material (M) is an organic semiconductor material.

In one embodiment, the material (M) is a plastic material, especially a transparent plastic material. For example said plastic material is a plastic film, especially a transparent plastic film.

In one embodiment, the material (M) is a conductive plastic.

The present invention thus also relates to a film, especially a transparent film, comprising at least one compound according to the invention.

There is no particular limitation on the method to produce a film. A film according to the invention generally comprises at least one polymer and/or polymeric material, and at least one compound according to the invention. Additional elements may be present in the film, without particular limitation.

According to the invention, the at least one compound according to the invention may be present in the film at various concentrations. Typically the concentration by weight of the at least one compound according to the invention is more than 0.01% with respect to the weight of the final film (w/w). This concentration may range from 0.05% to 90% (w/w). In one embodiment, the concentration of one or more compounds according to the invention is at least 0.5% (w/w).

Advantageously, the emission spectra of the fluorescent film can be tuned by changing the concentrations of the compound(s) according to the invention in the film. The invention therefore, relates to a dual light emitting film, more particularly to a white-light emitting film.

In one embodiment, the polymer is a conductive polymer.

In one embodiment, the polymer is an organic semiconductor polymer.

In one embodiment, the polymer is selected from the group consisting of: polymers containing acrylate-containing units, for example polyalkylacrylate, polyalkylmethacrylate especially polymethylmethacrylate (PMMA); polymers containing siloxane units, for example polyalkylsiloxane, especially polydimethylsiloxane (PDMS), polymers containing hydroxide groups-containing units, for example polyvinyl alcohol (PVA); polystyrene (PS); and any mixture thereof. In particular, the polymer is a mixture of PMMA and PS.

In one embodiment, the polymeric material is cellulose or latex.

A film can be prepared for example from a liquid phase containing at least one polymer and/or polymeric material suitable for forming a film and at least one compound according to the invention. A film may be prepared for example from such a liquid phase by evaporation, preferably slow evaporation, of the liquid phase to yield a film. Solvents of polymer and/or polymeric materials for preparing such a liquid phase are typically organic solvents but may also consist of or contain water. Typically, the liquid phase is a solution containing at least one polymer and/or polymeric material suitable for forming a film and at least one compound according to the invention. The liquid phase may also be a dispersion or an emulsion. Evaporation may be performed for example at room temperature in a container. If needed, the fluorescent film maybe subjected to further solvent elimination. For example the fluorescent film may be dried under vacuum, to remove remaining solvent.

Films can be shaped according to the techniques of the art. The shape of the transparent fluorescent films can be for example controlled by the shape of the container (glass sample tube: cylinder; glass plate substrate: quadrangle). Films can present a very wide range of thicknesses, typically from 10 nanometers (nm) to 1000 micrometers (µm) or more, preferably from 20 nm to 200 µm.

In one embodiment, the invention relates to a PMMA/PS film containing at least one compound according to the invention, for example at a concentration ranging from 0.5% (w/w) by weight with respect to the total film weight.

Light emission of the film may be obtained by excitation of the films by a physical stimulus, such as an electromagnetic radiation, typically a light radiation, a magnetic radiation or an electric radiation.

Upon photoexcitation, the inventors advantageously found that the compounds exhibit intense dual emission with contribution from the enol (E*) and the keto (K*) emission, K* being formed through excited state intramolecular proton transfer (ESIPT).

The ratio of dual emission intensity $R_{Du}$ may be defined in the present invention by the ratio between the intensity of the $\lambda_{max}$ (maximum emission wavelength) of the less intense emission band over the intensity of the $\lambda_{max}$ of the more intense emission band. For example, depending of the compound of the invention, the less intense emission band may be the one of the Enol form (E*) or the one of the Keto form (K*).

According to the invention, the compounds of the invention present significant dual emission properties when $R_{Du}$ is higher than 0.15, preferably higher than 0.2, and more preferably higher than 0.5. In particular, $R_{Du}$ is higher than 0.8.

Typically, ESIPT is a photophysical process that features a photoinduced proton transfer in the excited-state of specific π-conjugated compounds. The following scheme 1 is a representation of the ESIPT process in the compounds of the invention:

Scheme 1

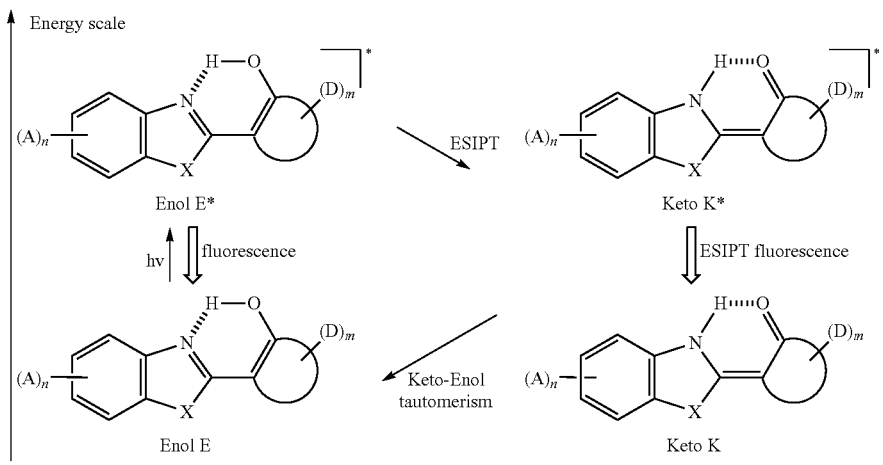

In particular in ESIPT process, upon absorption of light, a very fast phototautomerization process occurs (in the order of a sub-picosecond timescale) leading either to the sole emission of the tautomer or to a dual emission if the proton transfer is not quantitative. As a result of this sizeable reorganization of the molecular structure upon photoexcitation, large Stokes' shifts may be obtained due to the red-shifted emission of the keto tautomer (K*, in the case of a keto-enol tautomerism) as compared to that of the normal enol form (E*).

In particular, the inventors advantageously found that the ratio of emission intensity $R_{Du}$ is tunable. The compounds of the invention advantageously display broad and tunable dual emission.

The compounds according to the invention advantageously display dual emission, and more particularly white light emission, as a single compound in solution and/or in the solid state, and/or when incorporated in a material, such as a polymeric film or a solid material.

More particularly, the inventors found that when the compounds of the invention are in solution, they display dual emission in different type of solvents, such as protic and aprotic solvents.

Thus, the compounds according to the invention advantageously exhibit good luminescent properties, such as for example fluorescent or electroluminescent properties.

According to the CIE 1931 XYZ color space, created by the Commission Internationale de l'éclairage (CIE) in 1931, the CIE chromaticity coordinates for pure white light are (0.33, 0.33).

The compounds according to the invention provide an acceptable quantum yield, which is defined as the quotient of the number of photons emitted divided by the number of photons absorbed. The quantum yield represents the emission efficiency of a given compound.

An acceptable quantum yield is considered to be over 1.9%, preferably over 5%, and more preferably at least 10%. In particular, the quantum yield of the compounds of the invention is at least 15%.

In one embodiment, when the compounds of the invention are in solid-state, they exhibit a quantum yield higher than 7%, preferably at least 10%, and more preferably at least 20%.

Lifetime ($\tau$) is defined as the average length of time for the molecules to decay from one state to another. When a molecule absorbs a photon of appropriate energy, a chain of photophysical events ensues, such as internal conversion, fluorescence, intersystem crossing, and phosphorescence, as shown in the Jablonski diagram. Each of the processes occurs with a certain probability, characterized by decay rate constants (k).

Lifetime ($\tau$) is reciprocally proportional to the rate of decay: $\tau=1/k$. The lifetime can be considered as a state function because it does not depend on excitation wavelength.

The lifetime of a compound of the invention ranged typically from 0.2 to 10 nanoseconds, more specifically from 0.3 to 5 nanoseconds.

The present invention also relates to a light emitting device comprising at least one compound according to the invention, or a solid material (S) as defined according to the present invention or a material (M) as defined according to the present invention In one embodiment, the light emitting device is a luminescence device or an electroluminescence device.

Examples of light emitting device are Organic leds (OLEDs).

In one embodiment, the light emitting device is a white light emitting device. Example of such device is WOLED (White organic light emitting diodes).

The present invention also relates to a device for ratiometric analysis comprising at least one compound according to the invention or a solid state material (S) as mentioned above or a material (M) as mentioned above.

The ratio of the optical signals (at two distinct wavelengths) may be used to monitor the association equilibrium and to calculate analyte concentrations. Ratiometric measurements eliminate distortions of data caused by photobleaching and variations in probe loading and retention, as well as by instrumental factors such as illumination stability.

The present invention also relates to the use of at least one compound according to the invention, or a solid state material (S) as defined according to the present invention or a material (M) as defined according to the present invention, as fluorescent probe, in particular for ratiometric analysis. The compound according to the invention are thus useful for medical applications.

The present invention also relates to the use of at least one compound according to the invention, or a solid state material (S) as defined according to the present invention or a material (M) as defined according to the present invention, for emitting white light.

The inventors have discovered that the compounds according to the invention, namely compounds of formulae (I), (II), (III), (IV) and (V), and materials comprising them (for example film or solid material), advantageously exhibit dual emitting properties, and more particularly white light emitting properties.

The compounds according to the invention may also be used as pigments or dyes, in particular in paints or textiles, notably for clothes. In particular, the compounds are used in liquid or solid form, such as in powder form.

In one embodiment, the compounds according to the invention are encapsulated, notably in a matrix, such as an organic or polymeric matrix.

In one embodiment, the compounds according to the invention are used as pigment for security inks.

The security inks are well known by the skilled person. Security inks are typically used for security applications such as banknotes, official identity documents (passports, identity cards, birth certificates . . . ), postage stamps, tax banderoles, security labels and product markings.

Typically, the security inks fulfil the role of security in addition to their coloring function. In particular, the security inks can be used as anti-infringement labelling for different type of products or documents. In this particular case, the labelled product/document may be easily authenticated. In particular, the security inks are used for invisibly print security images having multiple authentication features.

In one embodiment, the present invention relates to security inks comprising at least one compound according to the invention, in particular the compounds being encapsulated such as in a organic or polymeric matrix.

EXAMPLES

The temperature is 25° C., unless contrary indicated.
The pressure is atmospheric pressure (101325 Pa), unless contrary indicated.
General Methods and Equipment:
All reactions were performed under a dry atmosphere of argon using standard Schlenck techniques. Dichloromethane were distilled over $P_2O_5$ under an argon atmosphere. Thin layer chromatography (TLC) was performed on silica gel or aluminium oxide ($Al_2O_3$) plates coated with fluorescent indicator. Chromatographic purifications were conducted using 40-63 μm silica gel. All mixtures of solvents are given in v/v ratio. The 300 ($^1H$), 400 ($^1H$), 75.46 ($^{13}C$), 100.3 ($^{13}C$) MHz NMR spectra were recorded at room temperature with perdeuterated solvents with residual protonated solvent signals as internal references. Mass spectra were measured with a ESI-MS mass spectrometer. Electronic absorption and emission spectra were measured under ambient conditions using commercial instruments Shimadzu UV3600 and Horiba Jobin-Yvon Fluoromax 4P. UV-Vis spectra were recorded using a dual-beam grating spectrophotometer with a 1 cm quartz cell. Fluorescence spectra were recorded with a spectrofluorimeter using typical Fluorescence software. Solvents for spectroscopy were spectroscopic grade and were used as received. Standard parameters were used for each instrument used. All fluorescence spectra were corrected from PM response. Luminescence lifetimes were measured on a spectrofluorimeter, using software with time-correlated single photon mode coupled to a Stroboscopic system. The excitation source was a laser diode (λ320 nm). The instrument response function was determined by using a light-scattering solution (LUDOX). The fluorescence quantum yield ($\phi_{exp}$) was calculated from eq (1).

$$\Phi_{exp} = \Phi_{ref} \frac{I}{I_{ref}} \frac{OD_{ref}}{OD} \frac{\eta^2}{\eta_{ref}^2} \quad (\text{eq 1})$$

I denotes the integral of the corrected emission spectrum, OD is the optical density at the excitation wavelength, and η is the refractive index of the medium. The reference systems used were rhodamine 6G, $\phi$=88% in ethanol $\lambda_{ex}$=488 nm for dyes emitting between 480 and 570 nm and quinine sulfate as reference $\phi$=0.55 in $H_2SO_4$ 1N, $\pi_{ex}$=366 nm for dyes emitting below 480 nm.

All chemicals were received from commercial sources (Aldrich, Alfa Aesar or Acros) and used without further purification. 4-(dimethoxy)phenyl acetylene and 4-(di-$^n$butylamino)phenyl acetylene were synthesized according to reported procedures (Feng et al., Org. Lett., 2013, 15, p. 936-939 and Miller et al., Synlett, 2004, 1, p. 165-168).

A. General Procedure for the Synthesis of salicylaldehydes (2), (3) and (4)

(1) and Pd(PPh$_3$)$_2$Cl$_2$ (5% molar) were dissolved in THF/triethylamine (3/1). The resulting suspension was degassed with argon for 30 minutes before the appropriate 4-substituted phenylacetylene (3 eq.) was added followed by CuI (10% molar). The resulting mixture was stirred overnight at 60° C. The dark solution was taken up in dichloromethane, washed with water, dried (MgSO$_4$) and concentrated in vacuo. The product was purified by silica gel chromatography (CH$_2$Cl$_2$/Pet. Ether 1:1) to afford clean salicylaldehyde (2), (3) or (4) after evaporation of the solvents in vacuo.

Example 1: Synthesis of the Intermediate 2,4-dihydroxy-5-iodobenzaldehyde (1)

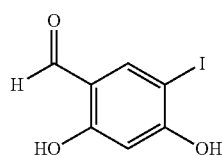 [SMILES: O=Cc1cc(I)c(O)cc1O]

2,4-Dihydroxy-5-iodobenzaldehyde (6 g, 43 mmol.) was dissolved in 50 mL of acetic acid. A solution of iodine monochloride (8,46 g, 52 mmol.) in 20 mL of acetic acid was added dropwise. The resulting mixture was stirred for 12 h at room temperature before it was poured into a saturated sodium thiosulfate solution (100 mL). The crude solution was extracted four times with ethyl acetate and the solvents were evaporated in vacuo. The crude residue was purified by silica gel chromatography eluting with CH$_2$Cl$_2$/ Pet. Ether 1:1 to CH$_2$Cl$_2$ 100% leading to compound 1 as white/beige powder (4.6 g, 40%). $^1$H NMR (300 MHz, d$_6$-acetone) δ (ppm): 11.07 (br s, 1H, OH), 10.73 (br s, 1H, OH), 9.76 (s, 1H, OH), 8.05 (s, 1H, CH Ar), 6.49 (s, 1H, CH Ar). $^{13}$C NMR (75 MHz, d$_6$-acetone) δ (ppm): 195.1, 164.9, 164.5, 145.7, 118.2, 103.1, 73.2.

Example 2: 2-(4-(tert-butyl)phenyl)-6-hydroxybenzofuran-5-carbaldehyde (2)

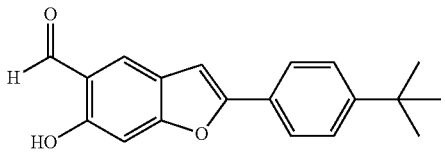 [SMILES: CC(C)(C)c1ccc(-c2cc3cc(C=O)c(O)cc3o2)cc1]

Beige powder. Yield: 56%. $^1$H NMR (300 MHz, CDCl$_3$) δ (ppm): 11.24 (s, 1H, OH), 9.92 (s, 1H, CHO), 7.70-7.76 (m, 3H, CH Ar), 7.07 (s, 1H, CH Ar), 6.92 (s, 1H, CH Ar), 6.48 (d, 2H, J=8.6 Hz, CH Ar), 1.36 (s, 9H, C(CH$_3$)$_3$). $^{13}$C NMR (75 MHz, CDCl$_3$) δ (ppm): 190.0, 160.3, 160.0, 157.7, 152.5, 127.0, 126.9, 126.0, 124.8, 123.3, 118.3, 100.2, 99.5, 35.0, 31.4. Anal. Calculated for C$_{19}$H$_{18}$O$_3$: C, 77.53; H, 6.16; Found C, 77.37; H, 5.97. EI-MS (m/z): 294.0.

Example 3: 6-hydroxy-2-(4-methoxyphenyl)benzofuran-5-carbaldehyde (3)

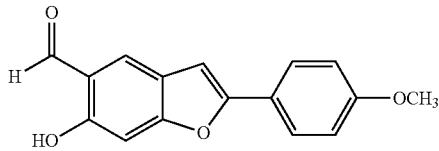 [SMILES: COc1ccc(-c2cc3cc(C=O)c(O)cc3o2)cc1]

Pale yellow powder. Yield: 60%. $^1$H NMR (300 MHz, CDCl$_3$) δ (ppm): 11.23 (s, 1H, OH), 9.92 (s, 1H, CHO), 6.67-7.76 (m, 3H, CH Ar), 6.97-7.05 (m, 3H, CH Ar), 6.83 (s, 1H, CH Ar), 3.87 (s, 1H, CH$_3$). $^{13}$C NMR (75 MHz, CDCl$_3$) δ (ppm): 196.0, 160.6, 160.3, 160.1, 157.7, 126.6, 123.5, 122.7, 118.4, 114.6, 99.5, 99.2, 55.6. Anal. Calculated for C$_{16}$H$_{12}$O$_4$: C, 71.64; H, 4.51; Found C, 71.79; H, 4.82. EI-MS (m/z): 268.0.

Example 4: 2-(4-(dibutylamino)phenyl)-6-hydroxybenzofuran-5-carbaldehyde (4)

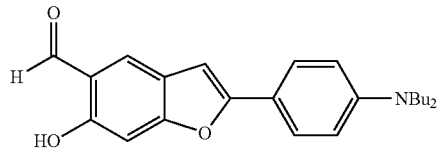

Orange powder. Yield: 44%. $^1$H NMR (300 MHz, CDCl$_3$) δ (ppm): 11.24 (s, 1H, OH), 9.87 (s, 1H, CHO), 7.57-7.64 (m, 3H, CH Ar), 7.02 (s, 1H, CH Ar), 6.65-6.69 (m, 3H, CH Ar), 3.32 (m, 4H, J=7.7 Hz, CH$_2$), 1.56-1.66 (m, 4H, CH$_2$), 1.33-1.45 (m, 4H, CH$_2$), 0.99 (t, 6H, J=7.4 Hz, CH$_3$). $^{13}$C NMR (75 MHz, CDCl$_3$) δ (ppm): 196.0, 159.9, 158.8, 148.8, 126.4, 125.7, 124.0, 117.7, 116.4, 111.6, 99.1, 96.7, 50.8, 29.6, 20.5, 14.1. Anal. Calculated for $C_{23}H_{27}NO_3$: C, 75.59; H, 7.45; N, 3.83; Found C, 75.34; H, 7.28; N, 3.50. EI-MS (m/z): 365.2.

B. Synthesis of Products

Route A: To a solution of 4'Bu-2-aminophenol in absolute ethanol was added salicylaldehyde ((2), (3) or (4)) (1 eq.). The mixture was refluxed for 5 h until an orange to red precipitate formed. After cooling down, the precipitate was filtered and redissolved in dry dichloromethane before 2,3-dichloro-5,6-dicyano-1,4-benzoquinone (DDQ) (1.2 eq.) was added as a concentrated dichloromethane solution. The resulting dark mixture was stirred at room temperature overnight. After solvent evaporation, the crude residue was purified by silica gel chromatography eluting with $CH_2Cl_2$/Pet. Ether 1:1.

Route B: To a solution of 4-substituted 2-aminophenol in methanol was added the appropriate salicylaldehyde ((2), (3) or (4)) (1 eq.), phenylboronic acid (1 eq.) and potassium cyanide (3 eq.). The resulting mixture was stirred for 12 hours at room temperature before the appearance of a precipitate. After solvent concentration in vacuo, the precipitate was filtered and further washed with EtOH and n-pentane.

Route C: Salicylaldehyde (4), 4-substituted 2-aminophenol (1 equiv), phenylboronic acid (1 equiv) and potassium cyanide (3 equiv) were stirred at room temperature in methanol for 12 hours. The solvents was evaporated in vacuo to dryness and purified on a silica column chromatography, using $CH_2Cl_2$/Petroleum ether as eluent to afford a the appropriate HBBO dye as a powder.

Example 5 (Comparative Example)

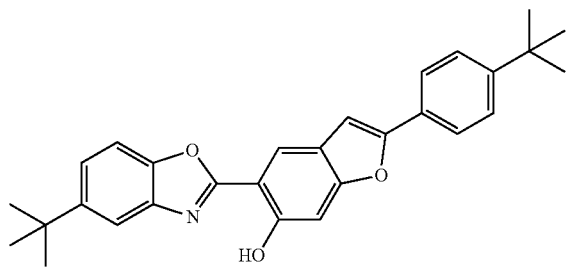 [SMILES: CC(C)(C)c1ccc(-c2cc3cc(-c4nc5cc(C(C)(C)C)ccc5o4)c(O)cc3o2)cc1]

Compound (5) was synthesized through Route A. Light yellow powder. Yield: 34%. $^1$H NMR (300 MHz, CDCl$_3$) δ (ppm): 11.76 (br s, 1H, OH), 8.20 (s, 1H, CH Ar), 7.78 (d, 2H, J=8.6 Hz, CH Ar), 7.42-7.54 (m, 5H, CH Ar), 7.23 (s, 1H, CH Ar), 6.95 (br s, 1H, CH Ar), 1.42 (s, 3H, –τBu), 1.37 (s, 3H, –τBu). $^{13}$C NMR (75 MHz, CDCl$_3$) δ (ppm): 158.4, 157.2, 156.8, 152.0, 148.8, 140.0, 127.5, 125.9, 124.7, 123.0, 122.7, 119.1, 115.8, 109.8, 107.7, 100.4, 99.6, 35.2, 34.9, 31.9, 31.4. Anal. Calculated for $C_{29}H_{29}NO_3$: C, 79.24; H, 6.65; N, 3.19; Found C, 79.04; H, 6.40; N, 2.99. EI-MS (m/z): 439.1.

Example 6 (Comparative Example)

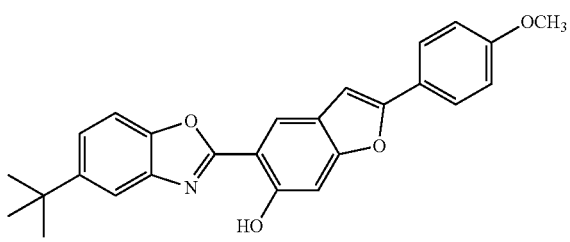 [SMILES: COc1ccc(-c2cc3cc(-c4nc5cc(C(C)(C)C)ccc5o4)c(O)cc3o2)cc1]

Compound (6) was synthesized through Route A. Light green powder. Yield: 42%. $^1$H NMR (300 MHz, CDCl$_3$) δ (ppm): 11.64 (br s, OH), 8.17 (s, 1H, CH Ar), 7.75-7.78 (m, 3H, CH Ar), 7.52 (d, 1H, J=8.8 Hz, CH Ar), 7.41-7.45 (dd, 1H, J=1.8 Hz, J'=8.6 Hz, CH Ar), 6.97 (d, 2H, J=8.8 Hz, CH Ar), 7.21 (s, 1H, CH Ar), 6.84 (s, 1H, CH Ar), 3.86 (s, 3H, CH$_3$), 1.42 (s, 9H, –τBu). $^{13}$C NMR (75 MHz, CDCl$_3$) δ (ppm): 163.7, 160.2, 158.3, 157.1, 156.7, 148.8, 147.2, 140.1, 126.4, 123.1, 123.0, 122.9, 118.8, 115.8, 114.4, 109.8, 107.7, 99.5, 99.3, 55.5, 35.2, 31.9. Anal. Calculated for $C_{26}H_{23}NO_4$: C, 75.53; H, 5.61; N, 3.39; Found C, 75.36; H, 5.37; N, 3.24. EI-MS (m/z): 413.1.

Example 7

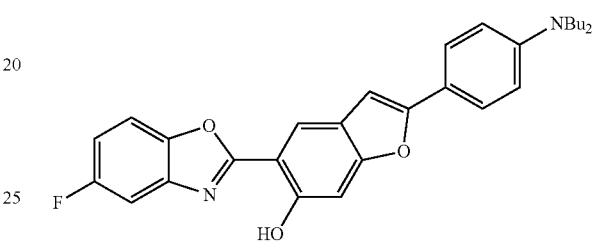

Compound (7) was synthesized through Route B. Brown-yellow powder. Yield: 25%. $^1$H NMR (300 MHz, CDCl$_3$) δ (ppm): 11.43 (s, 1H, OH), 8.11 (s, 1H, CH Ar), 7.65 (d, 2H, J=8.9 Hz, CH Ar), 7.55-7.51 (dd, 1H, J=4.2 Hz, J'=8.9 Hz, CH Ar), 7.42-7.39 (dd, 1H, J=2.7 Hz, J'=8.3 Hz, CH Ar), 7.19 (s, 1H), 7.09 (td, 1H, J=2.7 Hz, J=9.0 Hz, CH Ar), 6.67-6.71 (m, 3H, CH Ar), 3.35-3.30 (m, 4H, N—CH$_2$), 1.66-1.56 (m, 4H, CH$_2$), 1.44-1.32 (m, 4H, CH$_2$), 0.98 (t, 6H, J=7.9 Hz, CH$_3$). $^{13}$C NMR (75 MHz, CDCl$_3$) δ (ppm): 165.6, 158.5, 158.2, 156.8, 148.6, 145.6, 141.3, 141.1, 126.4, 123.6, 118.2, 117.0, 112.8, 112.4, 111.6, 111.0, 106.8, 105.9, 105.6, 99.5, 97.0, 50.9, 29.6, 20.5, 14.2. Anal. Calculated for $C_{29}H_{29}FN_2O_3$: C, 73.71; H, 6.19; N, 5.93; Found C, 73.49; H, 5.82; N, 5.64. EI-MS (m/z): 472.3 (100)

Example 8

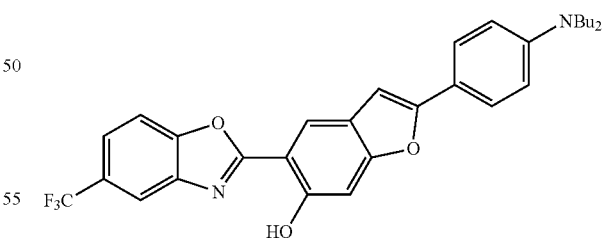

Compound (8) was synthesized through Route B. Yellow powder. Yield: 20%. $^1$H NMR (300 MHz, CDCl$_3$) δ (ppm): 11.31 (s, 1H, OH), 8.13 (s, 1H, CH Ar), 8.01 (s, 1H, CH Ar), 7.72-7.63 (m, 4H, CH Ar), 7.20 (1H, s, CH Ar), 6.71-6.67 (m, 3H, CH Ar), 3.35-3.30 (m, 4H, N—CH$_2$), 1.61 (m, 4H, CH$_2$), 1.44-1.32 (m, 4H, CH$_2$), 0.97 (t, 6H, J=7.2 Hz, CH$_3$). $^{13}$C NMR (75 MHz, CDCl$_3$) δ (ppm): Anal. Calculated for $C_{30}H_{29}F_3N_2O_3$: C, 68.95; H, 5.59; N, 5.36; Found C, 68.72; H, 5.34; N, 5.27. EI-MS (m/z): 523.4 (100)

Example 9

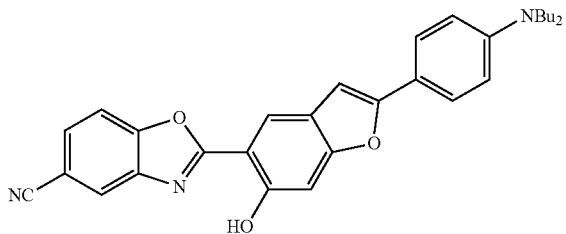

Compound (9) was synthesized through Route B. Brown-yellow powder. Yield: 45%. $^1$H NMR (300 MHz, CDCl$_3$) δ (ppm): 11.11 (s, 1H, OH), 8.07 (s, 1H, CH Ar), 7.99 (s, 1H, CH Ar), 7.68-7.62 (m, 4H, CH Ar), 7.17 (s, 1H), 6.68-6.66 (m, 3H, CH Ar), 3.32 (t, 4H, J=7.7 Hz, N—CH$_2$), 1.65-1.57 (m, 4H, CH$_2$), 1.43-1.34 (m, 4H, CH$_2$), 0.98 (t, 6H, J=7.3 Hz, CH$_3$). $^{13}$C NMR (75 MHz, CDCl$_3$) δ (ppm): 165.9, 158.9, 158.5, 157.0, 151.6, 148.7, 141.0, 129.2, 126.4, 123.9, 123.4, 118.5, 118.4, 116.7, 111.8, 111.6, 109.1, 105.9, 99.6, 96.7, 50.9, 29.6, 20.5, 14.2. Anal. Calculated for C$_{30}$H$_{29}$N$_3$O$_3$: C, 75.13; H, 6.10; N, 8.76; Found C, 74.84; H, 5.72; N, 8.54. EI-MS (m/z): 479.2 (100).

Example 10

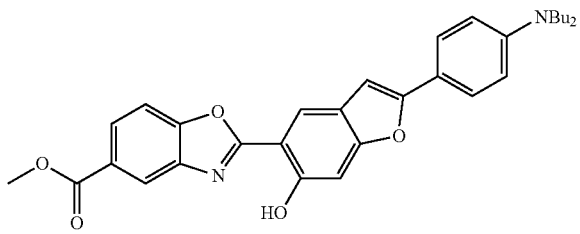

Compound (10) was synthesized through Route B. Yellow powder. Yield: 56%. $^1$H NMR (300 MHz, CDCl$_3$) δ (ppm): 11.39 (s, 1H, OH), 8.39 (s, 1H, CH Ar), 8.13-8.09 (m, 2H, CH Ar), 7.66-7.61 (m, 3H, CH Ar), 7.18 (s, 1H, CH Ar), 6.70-6.66 (m, 3H, CH Ar), 3.96 (s, 3H, OCH$_3$), 3.34-3.29 (m, 4H, N—CH$_2$), 1.65-1.55 (m, 4H, CH$_2$), 1.44-1.32 (m, 4H, CH$_2$), 0.98 (t, 6H, J=7.2 Hz, CH$_3$). $^{13}$C NMR (75 MHz, CDCl$_3$) δ (ppm): 166.7, 165.1, 158.6, 158.2, 156.8, 152.1, 148.6, 140.5, 127.5, 127.1, 126.4, 123.7, 120.9, 118.3, 116.9, 111.6, 110.4, 106.5, 99.5, 96.9, 50.9, 29.6, 20.5, 14.2. Anal. Calculated for C$_{31}$H$_{32}$N$_2$O$_5$: C, 72.64; H, 6.29; N, 5.47; Found C, 72.47; H, 6.04; N, 5.22. EI-MS (m/z): 512.1 (100).

The compounds 7 to 10 incorporate a strongly mesomeric electron-donating p-dibutylaminophenyl as a terminal group on the benzofuran moiety while the benzoxazole moiety is functionalized with several electron-withdrawing groups of increasing electronegativity (F, CF$_3$, CN or CO$_2$Me for compounds 7, 8, 9 and 10 respectively).

Example 11

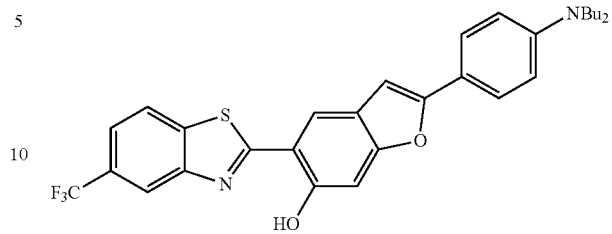

Compound (11) was synthesized through Route C. $^1$H NMR (400 MHz, CDCl$_3$): δ (ppm)=12.21 (s, 1H, OH), 8.22 (s, 1H, CH Ar), 7.98 (d, 1H, $^3$J=8.3 Hz, CH Ar), 7.76 (s, 1H, CH Ar), 7.66 (d, 2H, $^3$J=9.0 Hz, CH Ar), 7.62 (dd, 1H, $^3$J=8.4 Hz, $^4$J=1.7 Hz, CH Ar), 7.16 (s, 1H, CH Ar), 6.72 (d, 2H, $^3$J=8.2 Hz, CH Ar), 6.68 (s, 1H, CH Ar), 3.34 (t, 4H, $^3$J=7.4 Hz, CH$_2$), 1.67-1.59 (m, 4H, CH$_2$), 1.47-1.35 (m, 4H, CH$_2$), 0.99 (t, 6H, $^3$J=7.3 Hz, CH$_3$). $^{13}$C NMR (100 MHz, CDCl$_3$): δ (ppm)=172.4, 158.4, 156.5, 152.0, 148.8, 136.2, 129.6 (q, $^1J_{C-F}$=33.0 Hz), 126.5, 125.7, 123.9, 123.0, 122.1, 121.8 (q, $^3J_{C-F}$=3.7 Hz), 119.5, 119.2 (q, $^3J_{C-F}$=3.7 Hz), 117.3, 113.3, 112.0, 99.8, 96.9, 51.1, 29.7, 20.5, 14.1. Anal. Calculated for C$_{30}$H$_{29}$F$_3$N$_2$O$_2$S: C, 66.90; H, 5.43; N, 5.20. Found C, 66.83; H, 5.69; N, 4.97. EI-MS (m/z (relative intensity)): Theoretical mass 538.19 (100); Found 540.3 (9), 539.3 (28), 538.3 (80), 497.2 (6), 496.2 (21), 495.2 (65), 455.2 (9), 454.2 (27), 453.2 (100), 438.1 (32).

Example 12

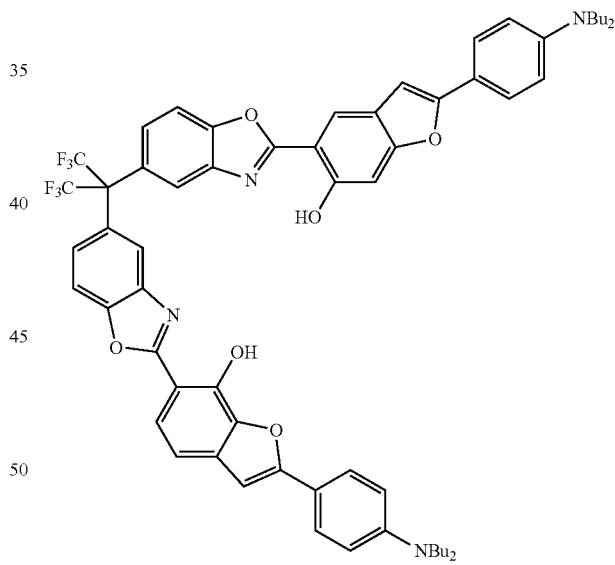

Compound (12) was synthesized through Route C. $^1$H NMR (300 MHz, CDCl$_3$): δ (ppm)=11.32 (s, 2H, OH), 8.10 (s, 2H, CH Ar), 7.91 (s, 2H, CH Ar), 7.66 (d, 4H, $^3$J=8.9 Hz, CH Ar), 7.59 (d, 2H, $^3$J=8.7 Hz, CH Ar), 7.43 (d$_t$, 2H, $^3$J=9.2 Hz, CH Ar), 7.17 (s, 2H, CH Ar), 6.70-6.67 (m, 6H, CH Ar), 3.32 (t, 8H, $^3$J=7.2 Hz, CH$_2$), 1.67-1.57 (m, 8H, CH$_2$), 1.46-1.34 (m, 8H, CH$_2$), 1.00 (t, 12H, $^3$J=7.3 Hz, CH$_3$). $^{13}$C NMR (75 MHz, CDCl$_3$): δ (ppm)=165.1, 158.6, 158.3, 156.9, 149.2, 148.7, 140.6, 130.6, 127.3, 126.3, 123.7, 122.6, 121.4, 118.3, 117.0, 11.6, 110.3, 106.6, 99.4, 96.9, 50.9, 29.6, 20.5, 14.1. Anal. calculated for C$_{61}$H$_{58}$F$_6$N$_4$O$_6$: C, 69.31; H, 5.53; N, 5.30. Anal. Found C, 69.05; H, 5.59; N, 5.23. EI-MS (m/z (relative intensity)): Theoretical mass 1056.43 (100); Found 1056.5 (24), 1013.4 (32), 443.4 (100).

Example 13

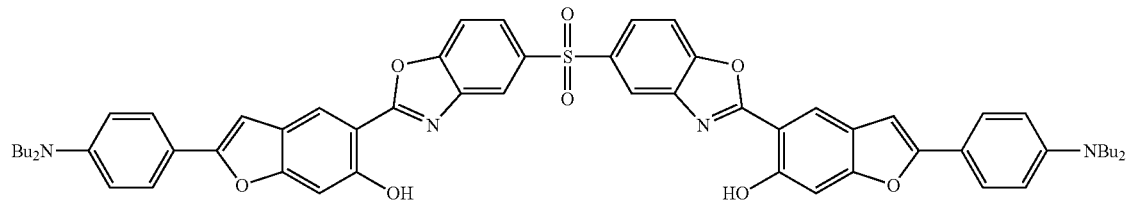

Compound (13) was synthesized through Route C. $^1$H NMR (400 MHz, CDCl$_3$): δ (ppm)=11.14 (s, 2H, OH), 8.36 (d, 2H, $^4$J=1.6 Hz, CH Ar), 8.07 (s, 2H, CH Ar), 8.04 (dd, 2H, $^3$J=8.5 Hz, $^4$J=1.7 Hz, CH Ar), 7.71 (d, 2H, $^3$J=8.6 Hz, CH Ar), 7.64 (d, 4H, $^3$J=8.8 Hz, CH Ar), 7.17 (s, 2H, CH Ar), 6.68-6.66 (m, 6H, CH Ar), 3.31 (t, 8H, $^3$J=7.3 Hz, CH$_2$), 1.63-1.56 (m, 8H, CH$_2$), 1.42-1.33 (m, 8H, CH$_2$), 0.97 (t, 12H, $^3$J=7.2 Hz, CH$_3$). $^{13}$C NMR (100 MHz, CDCl$_3$): δ (ppm)=166.1, 158.9, 158.5, 157.0, 151.9, 148.7, 141.2, 139.0, 126.4, 125.0, 123.9, 119.3, 118.4, 116.7, 111.6, 111.5, 106.0, 99.6, 96.8, 50.9, 29.6, 20.5, 14.1. Anal. calculated for C$_{58}$H$_{58}$N$_4$O$_8$S·CH$_2$Cl$_2$: C, 71.73; H, 6.02; N, 5.77. Anal. found C, 71.56; H, 6.04; N, 5.65. EI-MS (m/z (relative intensity)): Theoretical mass 970.40 (100); Found 972.5 (8), 971.5 (20), 970.5 (30), 928.5 (40), 927.4 (55), 400.8 (100).

Example 14

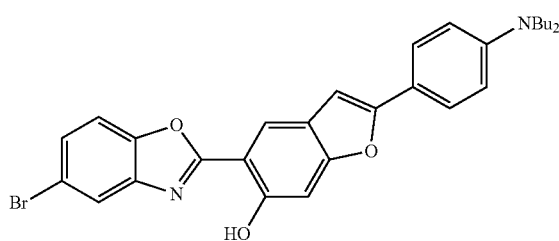

Compound (14) was synthesized through Route C. $^1$H NMR (400 MHz, CDCl$_3$): δ (ppm)=11.36 (s, 1H, OH), 8.10 (s, 1H, CH Ar), 7.86 (s, 1H, CH Ar), 7.66 (d, 2H, $^3$J=8.7 Hz, CH Ar), 7.47 (s, 2H, CH Ar), 7.18 (s, 1H, CH Ar), 6.70 (s, 1H, CH Ar), 6.68 (d, 2H, $^3$J=8.8 Hz, CH Ar), 3.32 (t, 4H, $^3$J=7.4 Hz, CH$_2$), 1.64-1.57 (m, 4H, CH$_2$), 1.43-1.34 (m, 4H, CH$_2$), 0.98 (t, 6H, $^3$J=7.3 Hz, CH$_3$). $^{13}$C NMR (100 MHz, CDCl$_3$): δ (ppm)=165.0, 158.6, 158.2, 156.8, 148.6, 148.3, 141.9, 128.1, 126.4, 123.7, 122.1, 118.3, 117.8, 116.9, 111.8, 111.6, 106.6, 99.5, 96.9, 50.9, 29.6, 20.5, 14.2. Anal. calculated for C$_{29}$H$_{29}$BrN$_2$O$_3$: C, 65.29; H, 5.48; N, 5.25. Anal. Found C, 65.41; H, 5.49; N, 5.22. EI-MS (m/z (relative intensity)): Theoretical Mass 532.14 (100); Found 535.2 (28), 534.2 (87), 533.2 (29), 532.2 (87), 492.2 (21), 491.2 (76), 490.2 (21), 489.2 (73), 450.1 (25), 449.1 (98), 448.1 (28), 447.1 (100).

Example 15

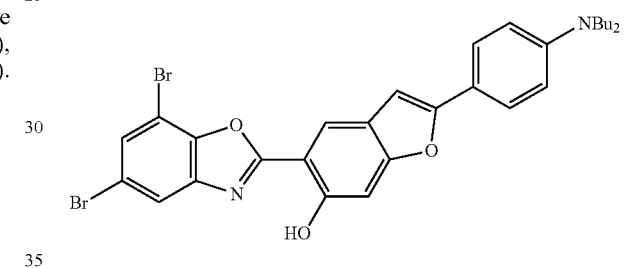

Compound (15) was synthesized through Route C. $^1$H NMR (300 MHz, CDCl$_3$): δ (ppm)=10.97 (s, 1H, OH), 7.91 (s, 1H, CH Ar), 7.65 (s, 1H, CH Ar), 7.56-7.50 (m, 3H, CH Ar), 7.06 (s, 1H, CH Ar), 6.62 (d, 2H, $^3$J=8.6 Hz, CH Ar), 6.56 (s, 1H, CH Ar), 3.30 (t, 4H, $^3$J=7.2 Hz, CH$_2$,), 1.66-1.56 (m, 4H, CH$_2$), 1.45-1.27 (m, 4H, CH$_2$), 0.99 (t, 6H, $^3$J=7.2 Hz, CH$_3$). $^{13}$C NMR (75 MHz, CDCl$_3$): δ (ppm)=164.8, 158.7, 158.2, 156.8, 148.6, 146.7, 142.0, 130.4, 126.2, 123.7, 121.0, 118.4, 117.9, 116.8, 111.5, 105.8, 103.2, 99.4, 96.7, 50.9, 29.6, 20.5, 14.1. EI-MS (m/z (relative intensity)): Theoretical mass 610.05 (100); Found 614.1 (47), 612.1 (88), 610.1 (47), 571.1 (40), 569.1 (80), 567.1 (40), 529.0 (53), 527.0 (100), 525.0 (49).

C. Photophysical Data

C.1. In Solution

Photophysical data in solution in various solvents were collected and are gathered in tables 1a and 1 b.

TABLE 1a

| | | | Optical data measured in solution | | | | | |
|---|---|---|---|---|---|---|---|---|
| Compounds | $\lambda_{abs}$ (nm) | ε (M$^{-1}$cm$^{-1}$) | $\lambda_{em}$ (nm) | $\Delta_{SS}$ (cm$^{-1}$) | $\phi_f^a$ | $R_{Du}$ | τ (ns) | Solvent |
| 5 (comparative) | 360 | 33500 | 546 | 9400 | 0.05 | | 0.4 | cyclohexane |
| | 361 | 37200 | 550 | 9500 | 0.07 | | 0.8 | toluene |
| | 358 | 33700 | 546 | 9600 | 0.04 | | 0.5 | CH$_2$Cl$_2$ |
| | 356 | 32600 | 546 | 9800 | 0.06 | | 0.3 | acetone |
| 6 (comparative) | 363 | 30600 | 546 | 9200 | 0.05 | | 0.6 | cyclohexane |
| | 364 | 33100 | 547 | 9200 | 0.06 | | 0.7 | toluene |
| | 361 | 32300 | 549 | 9500 | 0.05 | | 0.4 | CH$_2$Cl$_2$ |

TABLE 1a-continued

Optical data measured in solution

| Compounds | $\lambda_{abs}$ (nm) | $\epsilon$ (M$^{-1}$cm$^{-1}$) | $\lambda_{em}$ (nm) | $\Delta_{SS}$ (cm$^{-1}$) | $\phi_f{}^a$ | $R_{Du}$ | T (ns) | Solvent |
|---|---|---|---|---|---|---|---|---|
|   | 380 | 32600 | $^b$/557 | 8400 | 0.05 |   | 0.4/3.1 | acetone |
| 7 | 387 | 28200 | 450/560 | 3600 | 0.02/0.05 | 0.55 | 3.0/0.7 | cyclo-hexane |
|   | 389 | 29900 | 463/565 | 4100 | 0.02/0.08 | 0.41 | 3.6/0.7 | toluene |
|   | 386 | 30100 | 510/564 | 6300 | 0.08 | 0.83 | 0.9/4.4 | CH$_2$Cl$_2$ |
|   | 385 | 29000 | 500/588 | 6000 | 0.02 | 0.49 | 0.2/2.3 | EtOH |
| 8 | 391 | 30200 | 458/565 | 3700 | 0.10 | 0.69 | 0.4/0.4 | cyclo-hexane |
|   | 393 | 21300 | 468/568 | 4100 | 0.15 | 0.73 | 0.6/0.6 | toluene |
|   | 390 | 27100 | 522/560 | 6500 | 0.20 | 0.91 | 1.3 | CH$_2$Cl$_2$ |
|   | 389 | 27200 | 516/588 | 6300 | 0.02 | 0.74 | 0.3/2.5 | EtOH |
| 9 | 398 | 29300 | 463/562 | 3500 | 0.03/0.05 | 0.33 | 0.5 | cyclo-hexane |
|   | 396 | 28000 | 481/570 | 4500 | 0.05/0.05 | 0.73 | 0.8/0.8 | toluene |
| 10 | 388 | 32200 | 451/562 | 3600 | 0.08 | 0.50 | 0.3/0.3 | cyclo-hexane |
|   | 390 | 32700 | 467/569 | 4200 | 0.12 | 0.38 | 0.5/0.5 | toluene |
|   | 389 | 34700 | 515/570 | 6300 | 0.13 | 0.80 | 0.8/5.3 | CH$_2$Cl$_2$ |

[a] Quantum yields determined in solution, using quinine sulfate as reference $\phi$ = 0.55 in H$_2$SO$_4$ 1N, $\lambda_{ex}$ = 366 nm for dyes emitting below 480 nm, Rhodamine 6G $\phi$ = 0.88 in ethanol, $\lambda_{ex}$ = 488 nm for dyes emitting between 480 and 580 nm.
[b] broad shoulder
[c] not soluble.
[d] $R_{Du}$ = Intensity of $\lambda_{max}$ of less intense emission band/Intensity $\lambda_{max}$ of more intense emission band.

TABLE 2a

Optical data measured in solution

| Compounds | $\lambda_{abs}$ (nm) | $\epsilon$ (M$^{-1}$·cm$^{-1}$) | $\lambda_{em}$ (nm) | $\Delta$ (cm$^{-1}$) | $\phi_f{}^a$ | T (ns) | Solvent |
|---|---|---|---|---|---|---|---|
| 12 | 392 | 45000 | 455/567 | 3500 | 0.12 | 0.3/0.4 | cyclohexane |
|   | 394 | 61400 | 473/571 | 4200 | 0.06 | 0.6/0.5 | toluene |
|   | 392 | 62400 | 507/607 | 5800 | 0.03 | 0.3 | EtOH |
| 13 | 400 | 67500 | 478/574 | 4100 | 0.14 | 0.9/0.8 | toluene |
| 14 | 393 | 35900 | 453/557 | 3400 | 0.10 | 0.4 | cyclohexane |
|   | 394 | 32800 | 473/571 | 4200 | 0.09 | 0.6 | toluene |
|   | 389 | 13300 | 515/587 | 6300 | 0.03 | 0.2 | EtOH |
| 11 | 410 | 14500 | 485/609 | 3800 | 0.02 | 0.1 | cyclohexane |
|   | 413 | 25200 | 489/619 | 3800 | 0.01 | 0.1 | toluene |
| 15 | 402 | 28200 | 465/565 | 3400 | 0.09 | 0.6/0.6 | cyclohexane |
|   | 401 | 27800 | 481/570 | 4100 | 0.13 | 1.1/1.1 | toluene |

In view of table 1a, the compounds 5 and 6, which are not compounds according to the invention, do not exhibit dual emission in solution.

On the contrary, compounds according to the invention, namely compounds 7, 8, 9, 10, 11, 12, 13, 14 and 15 exhibit intense dual emission properties, as seen by the presence of two emission bands ($\lambda_{em}$) Such two emissions bands correspond to both the E* and the K* emissions bands. The intensity of the dual emission was measured with the $R_{Du}$ ratio, which is advantageously higher than 0.2, preferably higher than 0.3. Such results also indicate that the compounds 7, 8, 9, 10, 11, 12, 13, 14 and 15 display solution dual emissions in various type of solvent, such as for example solvents having low dielectric constant and high dielectric constant.

Compounds 8 and 9 exhibit the most intense dual emission where the maximum wavelength of the two bands E* and K* are the more strongly separated.

The results show that depending on the electronic substitution of the compounds, dual emission (both E* and K* bands) is observed, whose intensity ratio depends on the electronegativity of the electron-withdrawing group present on the compounds of the invention. This outcome is related to the relative excited state stabilities of the E* and K* tautomers.

It results from these experiment that the increase of the intensity of the E* band can be correlated to the global electronegativity of the fragment attached on the benzoxazole moiety of the compounds: from strongly electron-withdrawing (CF$_3$ and CN in compounds 8 and 9 respectively) to mildly electrowithdrawing (F and CO$_2$Me in compounds 7 and 10 respectively).

Without being bound by theory, it seems that the strong electron-donating ability of the p-dibutylaminophenyl group present on the compounds 7, 8, 9, 10, 11, 12, 13, 14 and 15, decrease the acidity of the benzofuran-ol moiety of the compounds, increasing its pKa which in turn stabilize the enol isomer in the excited stat. In addition, the presence of electron-withdrawing group on the benzoxazole moiety seems to increase the pKb of said benzoxazole moiety. These combined cooperative effects favor the obtaining of dual emission and allo to tune the $R_{Du}$ ratio.

In addition, due to the broad emission bands covering most of the visible range, white light emission was observed, notably in cyclohexane, notably for compounds 8, 9 and 10.

C.2. In Solid State

Photophysical properties were also investigated in the solid state dispersed in KBr matrix pellets and in PMMA/PS films. The optical properties are presented in tables 2a and 2b. The powders were dispersed in KBr matrix as pellets or dissolved as 0.5% in PMMA/PS and transparent polymer films were prepared on glass plates by spin coating method.

TABLE 2a

Optical data measured in the solid-state

| Compounds | $\lambda_{exc}$ (nm) | $\lambda_{em}$ (nm) | $R_{Du}{}^a$ | $\Delta_{SS}$ (cm$^{-1}$) | $\phi_f{}^b$ | x; y (CIE 1931) | Matrices |
|---|---|---|---|---|---|---|---|
| 5 (comparative) | 381 | 535 |   | 7600 | 0.54 | 0.401; 0.577 | KBr pellet |
|   | 360 | 546 |   | 9500 | 0.29 | 0.420; 0.536 | film |
| 6 (comparative) | 387 | 551 |   | 7700 | 0.31 | 0.465; 0.535 | KBr pellet |
|   | 363 | 544 |   | 9200 | 0.30 | 0.421; 0.540 | film |

TABLE 2a-continued

Optical data measured in the solid-state

| Compounds | $\lambda_{exc}$ (nm) | $\lambda_{em}$ (nm) | $R_{Du}{}^a$ | $\Delta_{SS}$ (cm$^{-1}$) | $\phi_f{}^b$ | x; y (CIE 1931) | Matrices |
|---|---|---|---|---|---|---|---|
| 7 | 400 | 476/571 | 0.35 | 4000 | 0.10 | 0.495; 0.458 | KBr pellet |
|  | 388 | 467/563 | 0.56 | 4400 | 0.30 | 0.386; 0.398 | film |
| 8 | 399 | 501/580 | 0.60 | 5100 | 0.19 | 0.353; 0.479 | KBr pellet |
|  | 399 | 481/561 | 0.99 | 4300 | 0.22 | 0.345; 0.398 | film |
|  | 395 | 493/560 | 0.81 | 5000 | 0.32 | 0.338; 0.430 | film |
| 10 | 386 | 481/564 | 0.60 | 5100 | 0.23 | 0.387; 0.418 | film |
|  | 386 | 481/564 |  | 5100 | 0.23 | 0.387; 0.418 | film |

[a] $R_{Du}$ = Intensity of $\lambda_{max}$ of less intense emission band/Intensity $\lambda_{max}$ of more intense emission band
[b] Absolute quantum yields determined using an integration sphere.

TABLE 2b

Optical data measured in the solid-state

| Compounds | $\lambda_{em}$ (nm) | $\phi_f{}^a$ | CIE Coordinates | Matrices |
|---|---|---|---|---|
| 12 | 463/568 | 0.37 | 0.38; 0.38 | PS |
|  | 469/566 | 0.38 | 0.36; 0.40 | PMMA |
| 13 | 482/570 | 0.68 | 0.32; 0.37 | PS |
|  | 485/569 | 0.39 | 0.34; 0.41 | PMMA |
| 14 | 505/586 | 0.11 | 0.37; 0.50 | KBr pellet |
|  | 466/570 | 0.42 | 0.39; 0.38 | PS |
|  | 465/566 | 0.33 | 0.38; 0.42 | PMMA |
| 11 | 525/646 | 0.22 | 0.60; 0.38 | KBr pellet |
| 15 | 479/579 | 0.50 | 0.31; 0.36 | PS |
|  | 481/561 | 0.38 | 0.34; 0.40 | PMMA |

The emission profiles recorded for compounds 7, 8, 9, 10, 11, 12, 13, 14 and 15 are following the same trends as those observed in the solution-state, i.e. a dual intense emission corresponding to the E* and K* bands at high and low energies respectively. For the comparative compounds 5 and 6, the emission spectra are quasi-identical as those recorded in solution with the sole K* band observed in KBr pellets and thin films of doped polymers respectively.

Besides, the quantum yields for compounds 7, 8, 9 and 10 are significantly higher than those recoded in solution spanning from 10 to 32%.

A more pronounced E* emission for compounds 8-9 bearing the strongest attracting groups (CN and CF$_3$ for 8 and 9 respectively) was recorded. It was observed that the intensity of the E* decreases along with the accepting ability of the group on the benzoxazole side; a feature found both in solution and in the solid-state.

In particular, the results show that as a consequence of the dual emission in the solid-state for compounds 7, 8, 9, 10, 11, 12, 13, 14 and 15, white light emission was observed in PMMA/PS doped films, especially for compound 8 whose CIE coordinates x;y are the closest to pure white (see table 2a).

These experimental results were also analyzed by Time-Dependent Density Functional Theory calculations (TD-DFT) that confirm that, on the one hand, only E* and K* emissions are present (no rotamer), and, on the other hand, the relative free energies of the two tautomers in the excited state guide the ratio of the E*/K* emission intensities.

It has been thus discovered that compounds according to the invention exhibit dual emission properties, in solution and/or especially in solid state.

It has been thus discovered that compounds according to the invention provide new white light emitting compounds.

It has been thus discovered that compounds according to the invention display broad and tunable dual emission upon photoexcitation.

It has been thus discovered that compounds according to the invention present good luminescent properties.

It has been thus discovered that compounds according to the invention present acceptable quantum yields.

The compounds according to the invention enable preparing devices for ratiometric detection and devices emitting white light.

D. Theoretical Calculations

Theoretical calculations were performed on the following compounds: B1, B2 and B3. B1 and B2 are comparative compounds, while compound B3 is a compound according to the invention.

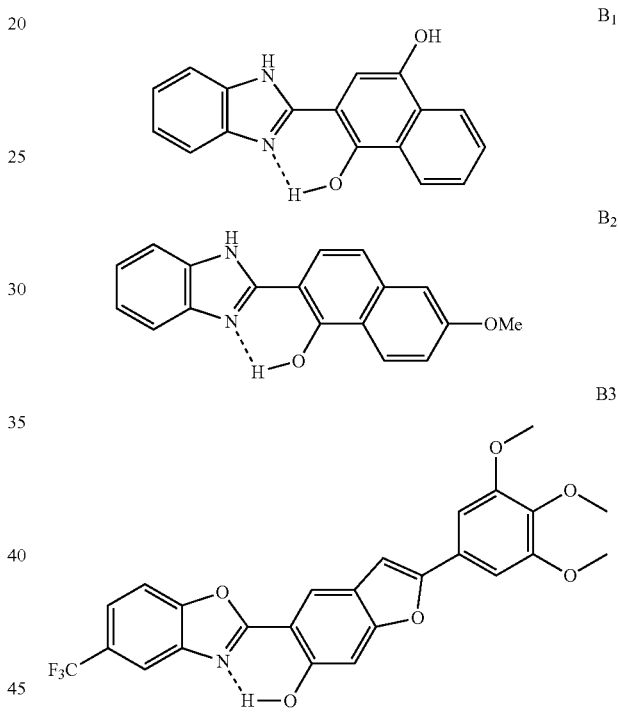

The protocol used here is PCM-M06-2X/6-31G(d), which allows the calculation of the Gibbs relative energies. Such protocol is disclosed in the publication Benelhadj, K. et al., "White emitters by tuning the excited state intramolecular proton transfer fluoresecence emission in 2-(2'-hydroxybenzofuran)benzoxazole dyes", Chemistry a European Journal, 2014, Sep. 21, 20(40), 12843-57.

For B$_1$, the enol conformation is favored by 7 kcal·mol$^{-1}$ in the ground state whereas the keto conformation is favored by 4 kcal·mol$^{-1}$ in the excited state. For B$_2$, the enol conformation is favored by 5 kcal·mol$^{-1}$ in the ground state whereas the keto conformation is favored by 4 kcal·mol$^{-1}$ in the excited state. For B$_3$, the enol conformation is favored by 14 kcal·mol$^{-1}$ in the ground state whereas the keto conformation is favored by 3 kcal·mol$^{-1}$ in the excited state.

The calculated excited-state delta G (eV) give −0.05 for B$_3$ which is very likely to display dual emission based on previous experimental/theory analogies.

B$_1$ and B$_2$ give −0.10 and −0.12 respectively which would be in favored of a single emission (quantitative proton transfer).

The invention claimed is:

1. A compound of formula (III):

(III)

wherein:
- $R_1$, $R_2$, $R_3$ and $R_4$ represent, independently of each other, H or an electron-withdrawing group A and at least one of $R_1$, $R_2$, $R_3$ and $R_4$ is the electron-withdrawing group A;
- $R_5$ and $R_8$ represent, independently of each other, H or an electron-donating group D;
- $R_9$ represents H;
- $R_{10}$ represents an aryl group comprising from 6 to 22 carbon atoms substituted with at least one electron donating group and
- X is selected from the group consisting of: O, S and NR, wherein R is selected from the group consisting of: H, an alkyl group, an aryl group, and a heteroaryl group.

2. The compound according to claim 1, wherein said compound presents the following formula (IV):

(IV)

wherein:
- $R_{11}$ represents an electron-donating group-D; and
- $R_1$, $R_2$, $R_3$, $R_4$, $R_5$, and $R_8$, are as defined in claim 1.

3. The compound according to claim 1, wherein said compound is a compound having the following formula (IV-bis):

(IV-bis)

wherein:
- $R_{12}$, $R_{13}$ and $R_{14}$, represent a same or different electron-donating group;
- $R_1$, $R_2$, $R_3$ and $R_4$ are as defined in claim 1; and
- $R_5$ and $R_8$ are as defined in claim 1.

4. The compound according to claim 1, wherein said compound presents the following formula (V):

(V)

wherein:
- R' and R" represent, independently of each other, H or an alkyl group;
- $R_5$, $R_8$ and X are as defined in claim 1; and
- $R_2$ is an electron-withdrawing group A.

5. The compound according to claim 1, wherein the electron-withdrawing group A is selected from the group consisting of:
- halogen;
- C(O)$R_e$, wherein $R_e$ is selected from the group consisting of Cl, H, an alkyl group and O$R_f$, wherein $R_f$ is H or an alkyl group;
- NO$_2$;
- SO$_2$NR$_g$R$_h$, R$_g$ and R$_h$ representing, independently of each other, an alkyl group or an aryl group;
- CN;
- CF$_3$;
- an alkyl group, substituted with at least one group selected from the group consisting of: halogen, NO$_2$, CN, C(O)R$_e$, SO$_2$NR$_g$R$_h$ and CF$_3$, wherein R$_e$, R$_g$ and R$_h$ are as defined above, said alkyl being optionally substituted with a heteroaryl, said heteroaryl being optionally substituted with a substituted heteroaryl;
- an aryl group, substituted with at least one group selected from the group consisting of halogen, NO$_2$, CN, C(O)R$_e$, SO$_2$NR$_g$R$_h$ and CF$_3$, wherein R$_e$, R$_g$ and R$_h$ are as defined above;
- —S(O)$_2$—W, wherein W is a heteroaryl optionally substituted with a substituted heteroaryl;
- SO$_3$H;
- a radical having a formula selected from the group consisting of:

wherein Ar is an aryl group; and $N^+R_iR_jR_h$, wherein $R_i$, $R_j$, and $R_k$ are, independently of each other, H or an alkyl group, said alkyl group being optionally substituted with at least one group selected from the group consisting of halogen, $NO_2$, CN, $C(O)R_e$, $SO_2NR_gR_h$ and $CF_3$, wherein $R_e$, $R_g$ and $R_h$ are as defined above.

6. The compound according to claim 5, wherein the electron-withdrawing group A comprises an π-electron conjugated chain.

7. The compound according to claim 1, wherein said electron-withdrawing group A is selected from the group consisting of:

C(O)H; C(O)OH; C(O)Cl; $NO_2$; $NH_4^+$; an aryl group comprising from 6 to 22 carbon atoms substituted with at least one nitro group, an aryl group comprising from 6 to 22 carbon atoms substituted with at least one CN; $CF_3$, C(O)OMe; F; Br;

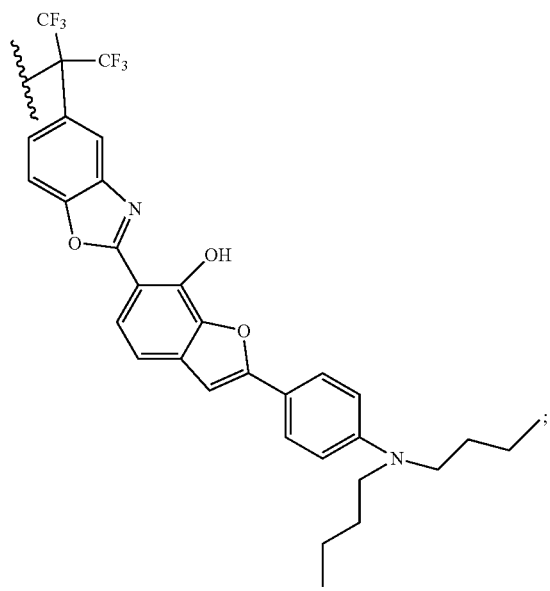

and

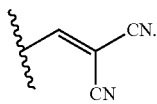

8. The compound according to claim 1, wherein said electron-withdrawing group A is:

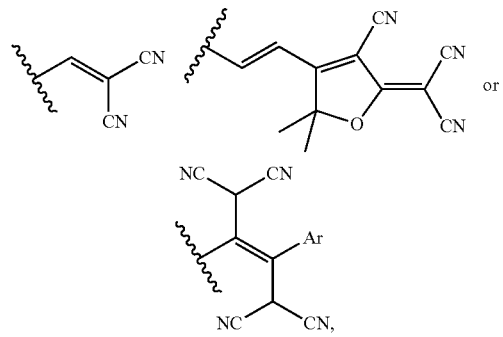

and wherein Ar is an aryl group.

9. The compound according to claim 1, wherein the electron-donating group D is selected from the group consisting of:

an alkyl group optionally substituted with at least one electron-donating group;

an aryl group optionally substituted with at least one electron-donating group;

$O^-$;

$OR_a$, wherein $R_a$ is H or an alkyl group;

$NR_bR_c$, wherein $R_b$ and $R_c$ are, independently of each other, selected from the group consisting of H, an alkyl group, and an aryl group; and $NHC(O)R_d$, wherein $R_d$ is selected from the group consisting of an alkyl group and an aryl group.

10. The compound according to claim 1, wherein $R_{10}$ represents a phenyl group substituted with at least one electron-donating group.

11. The compound according to claim 1, wherein $R_{10}$ represents a phenyl group substituted with at least one electron-donating group selected from the group consisting of $O^-$, $OR_a$, $NR_bR_c$ and —$NHC(O)R_d$, wherein $R_a$ is H or an alkyl group, wherein $R_b$ and $R_c$ are, independently of each other, selected from the group consisting of H, an alkyl group, and an aryl group and wherein $R_d$ is selected from the group consisting of an alkyl group and an aryl group.

12. The compound according to claim 1, wherein $R_{10}$ represents a phenyl group substituted with at least one $NR_bR_c$ group, wherein $R_b$ and $R_c$ are, independently of each other, selected from the group consisting of H, an alkyl group, and an aryl group.

13. The compound according to claim 1, wherein said compound is selected from the group consisting of:

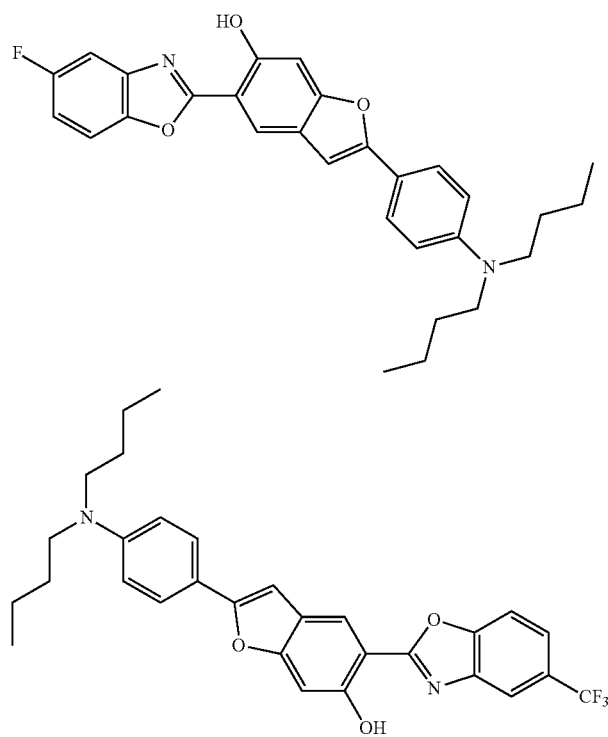
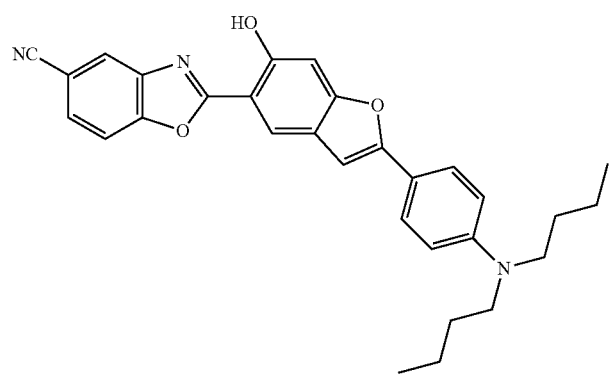
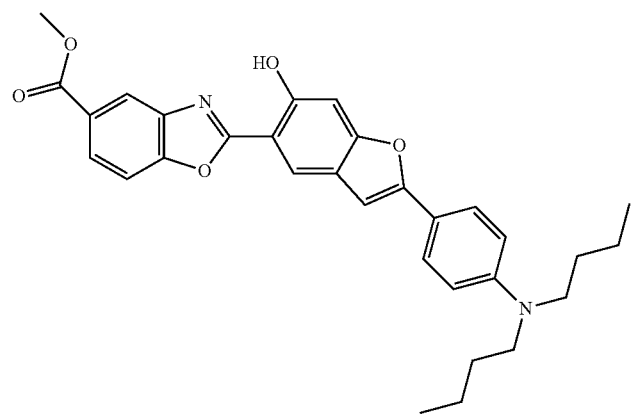

-continued
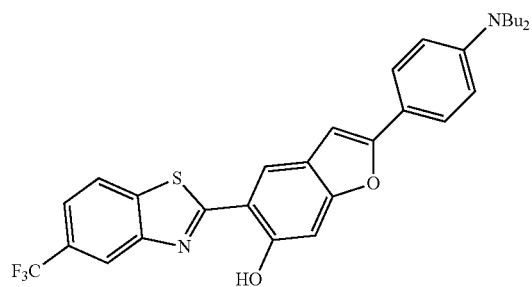
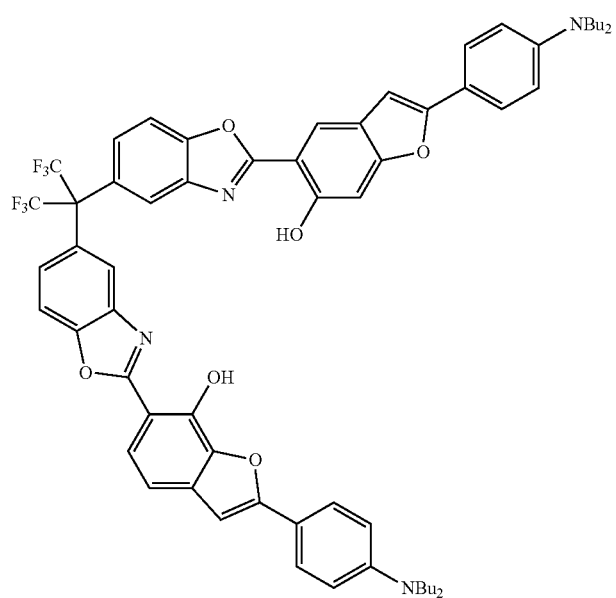
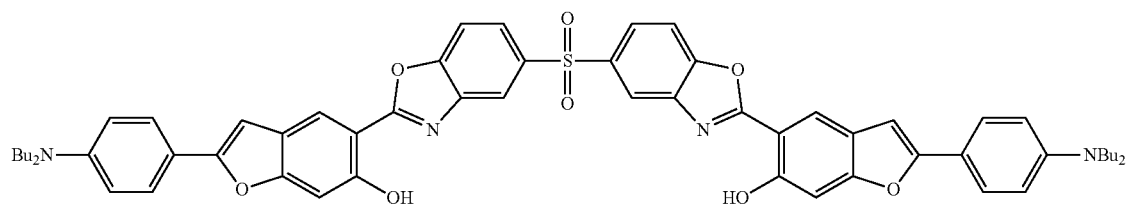
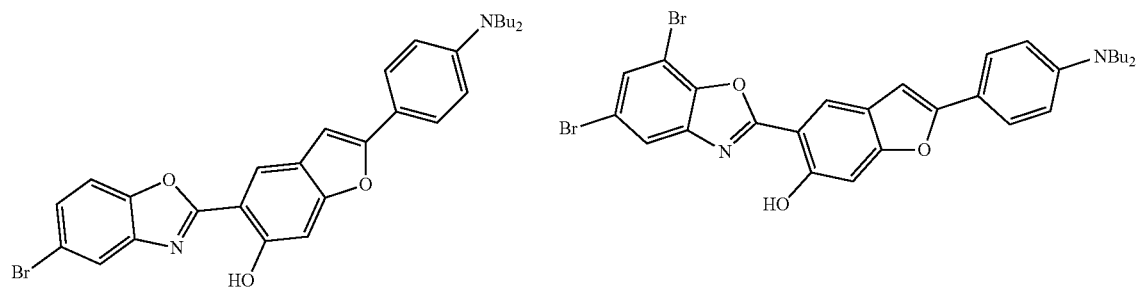

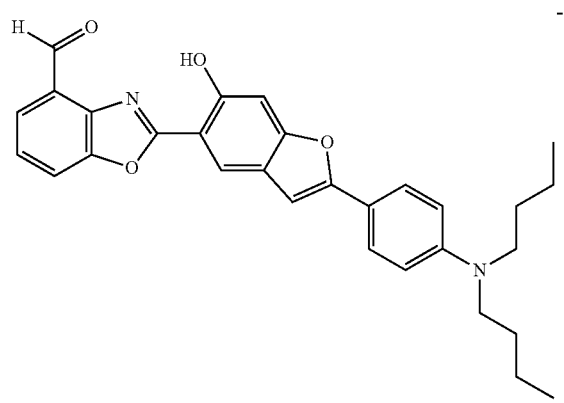
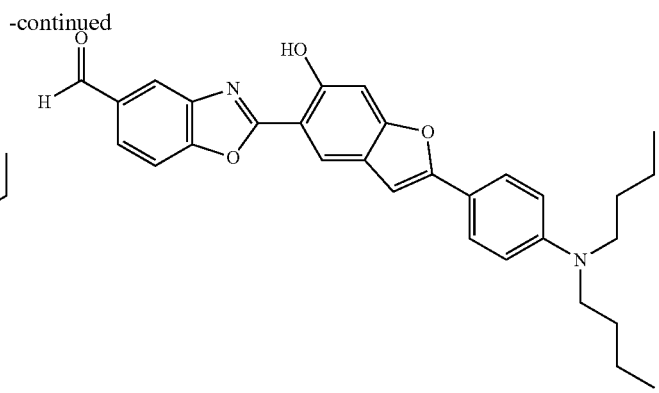

-continued

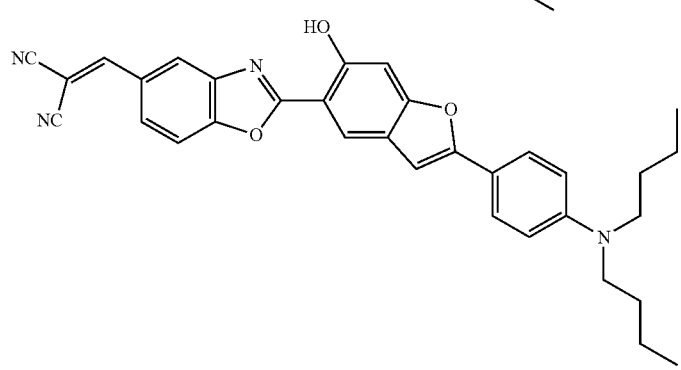

and

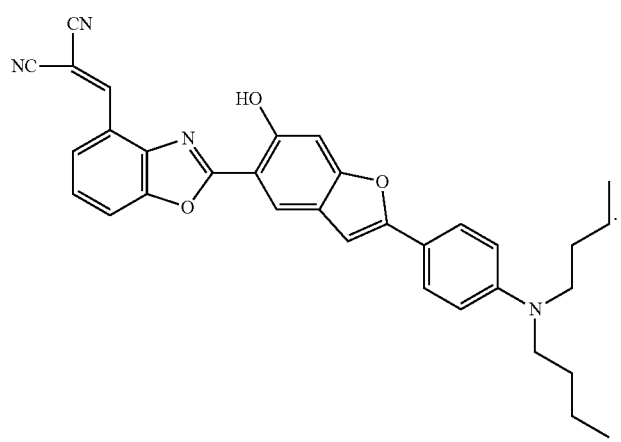

14. A solid material (S) comprising or consisting of at least one compound according to claim 1.

15. A material (M) comprising one or more compounds according to claim 1, and at least one polymer and/or at least one polymeric material and/or at least one organic matrix, said at least one organic matrix optionally comprising an inorganic material.

16. A light emitting device comprising at least one compound according to claim 1.

17. The light emitting device according to claim 16, wherein said at least one compound forms a solid material (S).

18. A device for ratiometric analysis comprising at least one compound according to claim 1.

19. The device for ratiometric analysis according to claim 18, wherein said at least one compound forms a solid material (S).

20. A method for emitting white light, said method comprising using at least one compound according to claim 1 for emitting white light.

21. A method for fluorescent probing, said method comprising using at least one compound according to claim 1 for fluorescent probing.

22. A compound of formula (III):

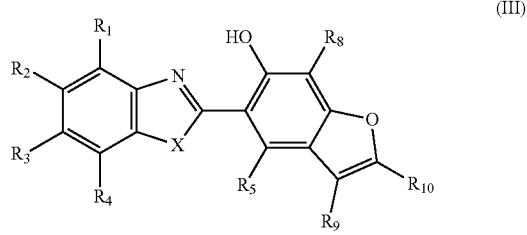

wherein:
- $R_1$, $R_2$, $R_3$ and $R_4$ represent, independently of each other, H or an electron-withdrawing group A and at least one of $R_1$, $R_2$, $R_3$ and $R_4$ is the electron-withdrawing group A;
- $R_5$ and $R_8$ represent, independently of each other, H or an electron-donating group D;
- $R_9$ represents H or an electron-donating group D;

R$_{10}$ represents a phenyl group substituted with —NR$_b$R$_c$, wherein R$_b$ and R$_c$ are, independently of each other, an alkyl group comprising from 1 to 20 carbon atoms; and X is selected from the group consisting of: O, S and NR, wherein R is selected from the group consisting of: H, an alkyl group, an aryl group, and a heteroaryl group.

23. The compound according to claim 22, wherein R$_b$ and R$_c$ are alkyl groups comprising 4 carbon atoms.

24. A device for light emitting or for ratiometric analysis, said device comprising at least one compound according to claim 22.

25. A method for emitting white light or for fluorescent probing, said method comprising using at least one compound according to claim 22 for emitting white light or for fluorescent probing.

* * * * *